(12) United States Patent
Hsu et al.

(10) Patent No.: US 11,623,951 B2
(45) Date of Patent: Apr. 11, 2023

(54) ANTIBODIES TO R-SPONDIN 3

(71) Applicant: National Health Research Institutes, Miaoli County (TW)

(72) Inventors: Tsu-An Hsu, Miaoli County (TW); Hui-Chen Hung, Miaoli County (TW); Teng-Yuan Chang, Miaoli County (TW); Chuan Shih, Carmel, IN (US)

(73) Assignee: National Health Research Institutes, Miaoli County (TW)

( * ) Notice: Subject to any disclaimer, the term of this patent is extended or adjusted under 35 U.S.C. 154(b) by 31 days.

(21) Appl. No.: 16/770,888

(22) PCT Filed: Dec. 6, 2018

(86) PCT No.: PCT/US2018/064236
§ 371 (c)(1),
(2) Date: Jun. 8, 2020

(87) PCT Pub. No.: WO2019/113306
PCT Pub. Date: Jun. 13, 2019

(65) Prior Publication Data
US 2021/0163580 A1    Jun. 3, 2021

Related U.S. Application Data

(60) Provisional application No. 62/595,845, filed on Dec. 7, 2017.

(51) Int. Cl.
*A61K 39/395* (2006.01)
*C07K 16/18* (2006.01)
*A61P 35/00* (2006.01)
*G01N 33/574* (2006.01)
*A61K 39/00* (2006.01)

(52) U.S. Cl.
CPC .............. *C07K 16/18* (2013.01); *A61P 35/00* (2018.01); *G01N 33/57496* (2013.01); *A61K 2039/505* (2013.01); *C07K 2317/24* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2009/0162353 A1 | 6/2009 | Johnson et al. |
| 2016/0002344 A1 | 1/2016 | Gurney et al. |
| 2017/0319688 A1 | 11/2017 | Storm |

FOREIGN PATENT DOCUMENTS

| | | |
|---|---|---|
| JP | 2016538832 A | 12/2016 |
| WO | WO-201412007 A1 | 8/2014 |
| WO | WO-2016090024 A2 | 6/2016 |
| WO | WO-2016/116760 A2 | 7/2016 |
| WO | WO-2017/180864 A | 10/2017 |
| WO | WO-2017180864 A1 | 10/2017 |

*Primary Examiner* — Christine J Saoud
(74) *Attorney, Agent, or Firm* — Cesari & McKenna, LLP

(57) ABSTRACT

Isolated antibodies that bind specifically to R-spondin 3 (RSPO3) are described. Also described herein are compositions containing the antibodies and methods of using the antibodies to treat cancer and detect RSPO3.

12 Claims, 21 Drawing Sheets

Specification includes a Sequence Listing.

FIG. 5

```
mRSPO3    (1)   MHLRLISCFFIILNFMEYIGSQNASRGRRQRRMHPNVSQGCQGGCATCSD
hRSPO3    (1)   MHLRLISWLFIILNFMEYIGSQNASRGRRQRRMHPNVSQGCQGGCATCSD 51                                              100
mRSPO3   (51)   YNGCLSCKPRLFFVLERIGMKQIGVCLSSCPSGYYGTRYPDINKCTKCKV
hRSPO3   (51)   YNGCLSCKPRLFFALERIGMKQIGVCLSSCPSGYYGTRYPDINKCTKCKA 101                                             150
mRSPO3  (101)   DCDTCFNKNFCTKCKSGFYLHLGKCLDSCPEGLEANNHTMECVSIVHCEA
hRSPO3  (101)   DCDTCFNKNFCTKCKSGFYLHLGKCLDNCPEGLEANNHTMECVSIVHCEV 151                                             200
mRSPO3  (151)   SEWSPWSPCMKKGKTCGFKRGTETRVRDILQHPSAKGNLCPPTSETRTCI
hRSPO3  (151)   SEWNPWSPCTKKGKTCGFKRGTETRVREIIQHPSAKGNLCPPTNETRKCT 201                                             250
mRSPO3  (201)   VQRKKCSKGERGKKGRERKRKKLNKEERKETSSSSDSKGLESSIETPDQQ
hRSPO3  (201)   VQRKKCQKGERGKKGRERKRKKPNKGESK--EAIPDSKSLESSKEIPEQR 251              278
mRSPO3  (251)   ENKERQQQKRRARDKQQKSVSVSTVH
hRSPO3  (249)   ENK--QQQKKRKVQDKQ-KSVSVSTVH
```

131R010

131R002 hybridoma A6

FIG. 15
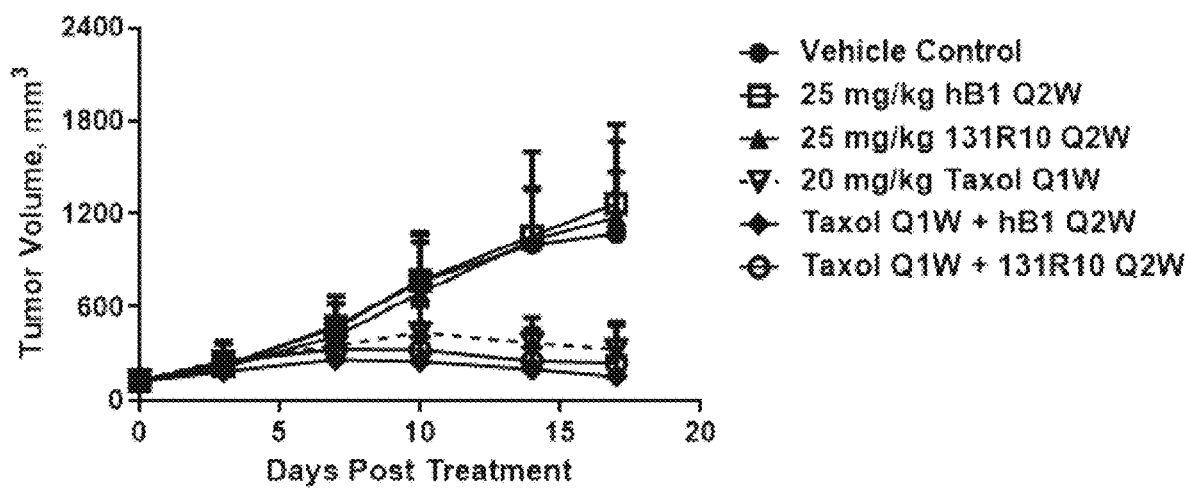
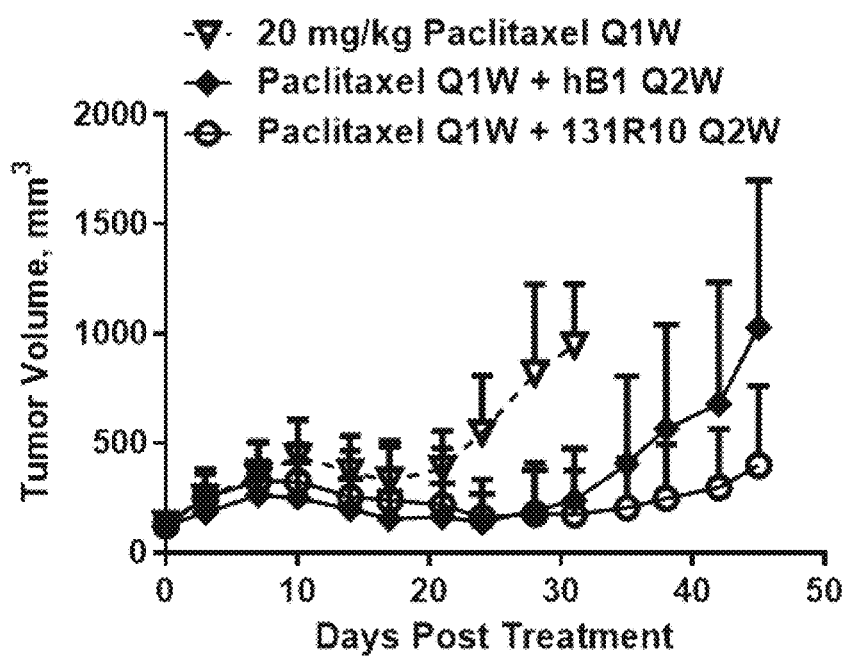

ANTIBODIES TO R-SPONDIN 3

CROSS REFERENCE TO RELATED APPLICATIONS

This application is the National Stage of International Application No. PCT/US2018/064236, filed on Dec. 6, 2018, which claims priority to U.S. Provisional Application No. 62/595,845, filed on Dec. 7, 2017, the contents of both prior applications being hereby incorporated by reference in their entirety.

BACKGROUND

R-spondins (RSPOs) are a group of four distinct secreted proteins (RSPO1, 2, 3, and 4), belonging to the superfamily of thrombospondin type 1 repeat (TSR-1)-containing proteins. See, e.g., Jin and Yoon (2012). The international journal of biochemistry & cell biology (44): 2278-2287. All human RSPOs share 40%-60% amino acid (a.a.) sequence similarity and these proteins contain 234 to 272 amino acids including the following elements: (i) an N-terminal hydrophobic signal peptide to promote the secretion of RSPOs; (ii) two furin-like cysteine-rich domains (FU-CRDs); (iii) a TSR-1 domain; and (iv) a C-terminal tail of basic amino acid-rich domain with positively charged residues. The two FU-CRDs were shown to be necessary and sufficient to promote Wnt/β-catenin-dependent signaling for the biological functions of RSPOs. See, e.g., de Lau et al. (2012). Genome biology (13): 242; and Kim et al. (2008). Molecular biology of the cell (19): 2588-2596. In contrast, the TSR-1 domain plays a mechanistic role in the regulation of Frizzled (Fz)/planar cell polarity (PCP) signaling.

RSPOs have pleiotropic functions in vertebrate development and stem cell growth. Several studies suggested that RSPOs can strongly enhance Wnt pathway signaling to result in activation of β-catenin with WNT ligands as can be explained by two possible models. See, e.g., Jin and Yoon (2012); de Lau et al. (2014). Genes & development (28): 305-316; and Kontermann, R. E. (2012). Archives of biochemistry and biophysics (526): 194-205. One model proposed that RSPOs bind directly to LRPS/6 and LGR4/5/6 receptors as activation ligands on the cluster of receptors with WNT and FZD to activate Wnt/b-catenin signaling in cancer. See, e.g., Wang et al. (2013). Genes & development (27): 1339-1344. Alternatively, RSPOs may also antagonize DKK1-mediated endocytosis by interfering with DKK1-mediated LRP6 and Kremen association. RSPOs bind to the ZNFR3 and its homologue RNF43 as negative feedback regulators to accelerate the FZD and LRP6 receptors turnover on the cell surface in another model. See, e.g., Jin and Yoon (2012).

WNT signaling is involved in the regulation of cell proliferation, differentiation, migration, and survival. See, e.g., Niehrs (2012). Nature reviews. Molecular cell biology (13): 767-779. Thus, Wnt signaling pathway has been investigated as a potential target for cancer therapy. See, e.g., Madan and Virshup (2015). Molecular cancer therapeutics (14): 1087-1094. Human genetics studies and gene targeting approaches demonstrated that RSPOs have the ability to be canonical and non-canonical WNT regulators. MacDonald et al. (2009). Developmental cell (17): 9-26. Gain of function of RSPO3 gene fusions enhanced FZD and LRPS/6 cell surface abundance and, in turn, activated Wnt signaling. Madan et al. (2015). Oncogene (35): 2197-2207. A subset of patients with difficult-to-treat cancers were shown to carry RSPO-fused genes. See, e.g., Madan et al. (2015). For example, the protein tyrosine phosphatase receptor type K was found to fuse with RSPO3 to form (PTPRK)-RSPO3 fusion in 5-10% of colon cancers. See, e.g., Seshagiri et al. (2012). Nature (488): 660-664. Activated Wnt signaling was found in 10% of APC$^{wild-type}$ colon cancers and 1-11% of ovarian, esophageal, lung and head and neck cancers. See, e.g., Seshagiri et al. (2012). Approximately 1~2% of a 324 NSCLC cohort were diagnosed with EIF3E(e1)-RSPO2(e1), and PTPRK(e1)-RSPO3(e2), and PTPRK(e7)-RSPO3(e2). See, e.g., Browning et al. (2001). Trends in biochemical sciences (26): 284; and Parker and Zhang (2013). Chinese journal of cancer (32): 594-603. Two recent studies have demonstrated that anti-RSPO3 antibodies have antagonistic activity on tumors with RSPO3-fusion gene or RSPO3-stimulating beta-catenin signaling. See, e.g., Storm et al. (2016). Nature (529): 97-100; and Chartier et al. (2016). Cancer research (76): 713-723. Thus, there appears to be a subset of cancers driven by enhanced RSPO-Wnt signaling. Anti-RSPO3 antibodies have the potential to significantly impact anti-cancer therapy in a variety of cancers including colon, lung, and ovarian cancers.

SUMMARY

In one aspect, described herein is an isolated antibody. The isolated antibody contains heavy chain complementary determining regions CDR1, CDR2, and CDR3 derived from a heavy chain variable region sequence selected from SEQ ID NOs: 2, 6, 10, and 14; and light chain complementary determining regions CDR1, CDR2, and CDR3 derived from a light chain variable region sequence selected from SEQ ID NOs: 4, 8, 12, and 16; wherein the antibody binds specifically to a RSPO3 protein.

In some embodiments, the heavy chain CDR1, CDR2, and CDR3 are derived from SEQ ID NO: 2, and the light chain CDR1, CDR2, and CDR3 are derived from SEQ ID NO: 4.

In some embodiments, the antibody includes a heavy chain variable region that is at least 80% identical to the sequence of SEQ ID NO: 2, and a light chain variable region that is at least 80% identical to the sequence of SEQ ID NO: 4.

In some embodiments, the heavy chain CDR1, CDR2, and CDR3 are derived from SEQ ID NO: 6, and the light chain CDR1, CDR2, and CDR3 are derived from SEQ ID NO: 8. The antibody can include a heavy chain variable region that is at least 80% (e.g., 85%, 90%, 95%, 96%, 97%, 98%, 99%, or 100%) identical to the sequence of SEQ ID NO: 6, and a light chain variable region that is at least 80% (e.g., 85%, 90%, 95%, 96%, 97%, 98%, 99%, or 100%) identical to the sequence of SEQ ID NO: 8.

In some embodiments, the heavy chain CDR1, CDR2, and CDR3 are derived from SEQ ID NO: 10, and the light chain CDR1, CDR2, and CDR3 are derived from SEQ ID NO: 12. The antibody can include a heavy chain variable region that is at least 80% (e.g., 85%, 90%, 95%, 96%, 97%, 98%, 99%, or 100%) identical to the sequence of SEQ ID NO: 10, and a light chain variable region that is at least 80% (e.g., 85%, 90%, 95%, 96%, 97%, 98%, 99%, or 100%) identical to the sequence of SEQ ID NO: 12.

In some embodiments, the heavy chain CDR1, CDR2, and CDR3 are derived from SEQ ID NO: 14, and the light chain CDR1, CDR2, and CDR3 are derived from SEQ ID NO: 16. The antibody can include a heavy chain variable region that is at least 80% (e.g., 85%, 90%, 95%, 96%, 97%, 98%, 99%, or 100%) identical to the sequence of SEQ ID NO: 14, and a light chain variable region that is at least 80%

(e.g., 85%, 90%, 95%, 96%, 97%, 98%, 99%, or 100%) identical to the sequence of SEQ ID NO: 16.

The antibody described herein can bind to a conformationally-determined or linear epitope in the RSPO3 protein. It can be an IgG antibody, an antibody that contains an Fc region, an Fab fragment, an Fab' fragment, an F(ab')$_2$ fragment, a single-chain antibody, an scFV multimer, a monovalent antibody, a multivalent antibody, or a chimeric antibody.

In some embodiments the antibody is humanized. In some embodiments, the antibody is conjugated to another molecule (e.g., a small molecule drug, a cell-targeting moiety, a cytotoxic agent, an immunomodulator, a polypeptide, a nucleic acid molecule, a detectable label, or a polymer) to generate an immunoconjugate.

Also described herein is an isolated nucleic acid molecule containing a nucleic acid sequence that encodes any of the antibodies disclosed herein.

In another aspect, provided herein is a host cell that contains the isolated nucleic acid.

In one aspect, a composition containing the antibody described herein is described. The composition can further include a pharmaceutically acceptable carrier and/or another therapeutic agent (e.g., another cancer drug, a cytotoxic agent, or an immunomodulator).

Any of the antibodies described herein can be used to inhibit RSPO3 or Wnt signaling in a cell by contacting the cell with an effective amount of the antibody.

The antibody can also be used to inhibit cancer cell growth or cancer cell metastasis by contacting the cell with an effective amount of the antibody.

In yet another aspect, described herein is a method of treating a cancer in a subject, including administering to the subject an effective amount of any of the antibodies disclosed herein.

In some embodiments, the cancer is a RSPO3 positive cancer, a RSPO3-fusion positive cancer, a cancer with an adenomatous polyposis coli (APC) mutation, or a cancer with a β-catenin mutation, or a cancer with hyperactivated Wnt signaling. In some embodiments, the method further includes, prior to administering the antibody to the subject, determining whether the cancer in the subject has one of the above mutations or aberrations. The cancer can be colon cancer, leukemia, colorectal cancer, ovarian cancer, pancreatic cancer, lung cancer, liver cancer, breast cancer, kidney cancer, prostate cancer, gastrointestinal cancer, melanoma, cervical cancer, bladder cancer, glioblastoma, or head and neck cancer. In some embodiments, the method further includes administering another therapeutic agent to the subject.

Also provided herein is a method of detecting a RSPO3 protein or a fragment thereof in a sample. The method includes contacting the sample with any of the antibodies described herein and assaying for specific binding between the antibody and a RSPO3 protein or a fragment thereof. In some embodiments, the RSPO3 protein is human RSPO3.

A method of identifying an antibody variant that specifically binds to an RSPO3 protein is described herein. The method includes introducing one or more modifications in the one or more complementary determining regions of an antibody described herein to produce an antibody variant; and identifying an antibody variant that specifically binds to an RSPO3 protein.

The details of one or more embodiments are set forth in the accompanying drawing and the description below. Other features, objects, and advantages of the embodiments will be apparent from the description and drawing, and from the claims.

BRIEF DESCRIPTION OF DRAWINGS

FIG. 5 is an alignment of the amino acid sequences of hRSPO3 and mRSPO3.

FIG. 15 is a set of graphs showing anti-tumor efficacy of in human SNU-1411 colon xenograft tumor carrying PTPRK(e13)-RSPO3(e2) fusion transcript. Tumor cells were injected into the mice and treatments were initiated when the tumors reaches 200 mm$^3$. Antibodies were given at 25 mg/kg once every other week (Q2W) and paclitaxel at 20 mg/kg once every week (Q1W). Both antibodies and carboplatin were administered by intravenous injection. Paclitaxel was given from day 1 to day 32 and combination groups from day 1 to day 46. Both antibodies and paclitaxel were administered by intravenous injection. For each treatment cycle, antibodies were given on day 1 and paclitaxel on day 3. Tumor and body weight measurements were taken on the indicated days. Mean±SEM. *: p<0.05 vs. control mAb by one-way ANOVA followed by Tukey's post-test comparison.

DETAILED DESCRIPTION

Figure 1:
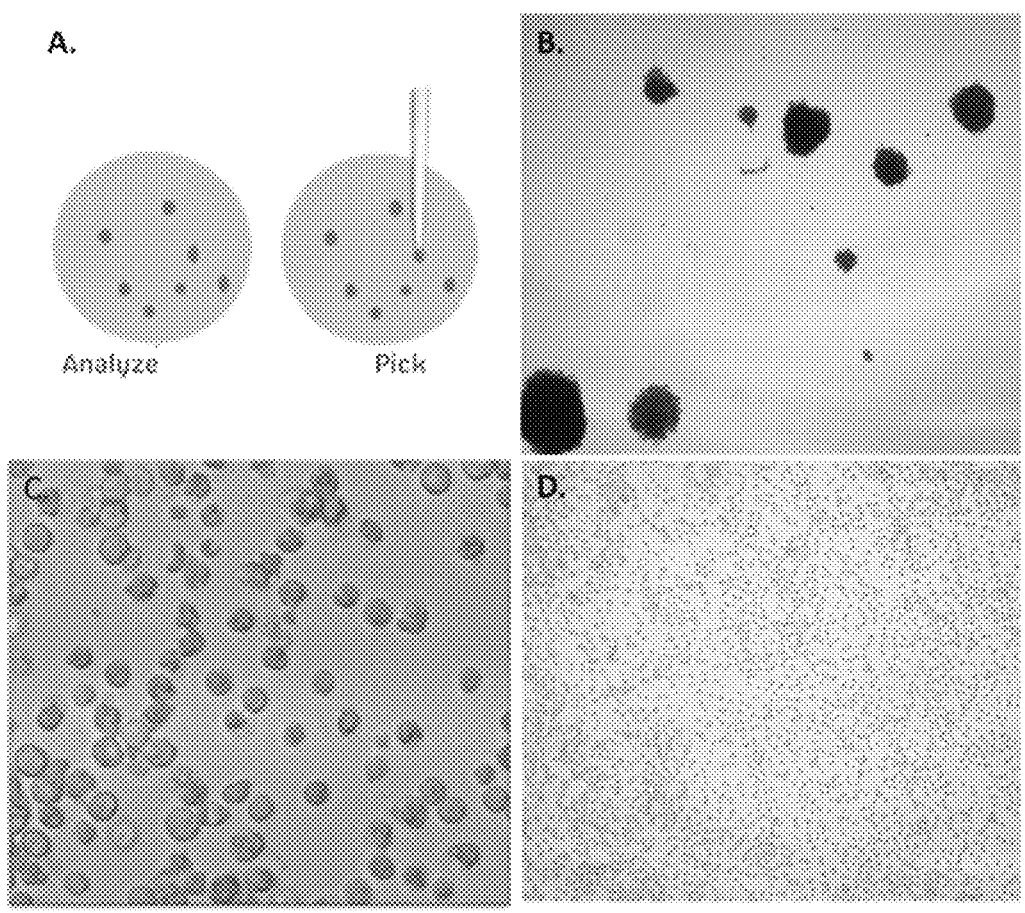
FIG. 1 is a set of schematic diagrams and images showing use of RSPO3 Hybridoma B1 as a model for screening single cell lines. (A) Schematic diagrams show the single colony selection procedure; (B) Single clones were identified by limiting dilution and expansion; (C) The clones were transferred and assessed for Ab expression; and (D) Cells that exhibit high Ab expression levels were expanded in T25-cm$^2$ tissue culture flasks.

Described herein are novel anti-RSPO3 antibodies. In particular, the humanized antibody hB1 demonstrated in vitro and in vivo anti-cancer efficacy in cancers with RSPO3-fusion genes or RSPO3 overexpression. Data described below demonstrate that: (1) The binding affinity of hB1 to RSPO3 is in the pM range; (2) In a β-catenin TCF/LEF-Luc reporter system, hB1 and rosmantuzumab showed equal potency; (3) hB1 and rosmantuzumab showed equal anti-cancer efficacy in the CR3150 colorectal cancer PDX model; (4) hB1 showed anti-cancer efficacy in the NCI-H2030 and SNU-1411 cancer xenograft models; (5) hB1 can be used for determining RSPO3 levels in samples; and (6) hB1 and rosmantuzumab bind to different epitopes.

The sequences of the heavy chain and light chain variable regions of antibodies A4, A6, B1, and hB1 are shown in the tables below. The complementary determining regions (CDRs) predicted by 4 different methods (IMGT, Chothia, KABAT, and Honegger) are also shown in the tables.

| Antibody A4 |
| --- |
| Heavy chain variable region |

SEQ ID NO: 1    CAGGTGCAACTGCAGGAGTCTGGGGCTGAACTGGCAAAACCTGGGGCCTCAGTGAAGATGTCC
TGCAAGGCTTCTGGCCACACTCTAACTTACTACTGGATGCACTGGGTAAAACAGAGGCCTGGAC
AGGGTCTGGAATGGATTGGATACATTGATCCTAGCACTGGTTATAGTGAATACAATCAAAGATT
CGAGGGCAAGGCCACATTGACTGCAGACAAGTCCTCCGGCACAGTCTACATGCAGCTGAGCAG
CCTGACATCTGAGGACTCTGCGGTCTATTACTGTGCAAGAAACGGGCCCTTTGCTTACTGGGC
CAAGGGACTCTGGTCACTGTCTCTGCG

SEQ ID NO: 2    QVQLQESGAELAKPGASVKMSCKASGHTLTYYWMHWVKQRPGQGLEWIG**YIDPSTGYSEYNQR
FEGKATLTADKSSGTVYMQLSSLTSEDSAVYYCARNGPFAY**WGQGTLVTVSA

IMGT            QVQLQESGAELAKPGASVKMSCKASGHTLTYYWMHWVKQRPGQGLEWIGYIDPSTGYSEYNQR
FEGKATLTADKSSGTVYMQLSSLTSEDSAVYYCARNGPFAYWGQGTLVTVSA

Chothia         QVQLQESGAELAKPGASVKMSCKASGHTLTYYWMHWVKQRPGQGLEWIGYIDPSTGYSEYNQR
FEGKATLTADKSSGTVYMQLSSLTSEDSAVYYCARNGPFAYWGQGTLVTVSA Kabat           QVQLQESGAELAKPGASVKMSCKASGHTLTYYWMHWVKQRPGQGLEWIG**YIDPSTGYSEYNQR
FEGKATLTADKSSGTVYMQLSSLTSEDSAVYYCARNGPFAYWGQGTLVTVSA Honegger        QVQLQESGAELAKPGASVKMSCKASGHTLTYYWMHWVKQRPGQGLEWIGYIDPSTGYSEYNQR
FEGKATLTADKSSGTVYMQLSSLTSEDSAVYYCARNGPFA**YWGQGTLVTVSA

| Light chain variable region |
| --- |

SEQ ID NO: 3    GACAATGTTCTCACCCAGTCTCCAGCAATCATGTCTGCATCTCCAGGGGAGAAGGTCACCATGA
CCTGCAGTGCCAGCTCAAGTGTAAATTACATGTACTGGTACCAGCAGAAGCCGGGATCCTCCCC
CAGACTCCTGATTTATGACACATCCAAGCTGGCTTCCGGAGTCCCTGTTCGCTTCAGTGGCAGT
GGGTCTGGGACCTCTTACTCTCTCACAATCAGCCGAATGGAGGCTGAAGATGCTGCCACTTATT
ATTGCCAGCAGTGGAGTAGTTCCCCGCTCACGTTCGGTGTTGGGGCCAAGCTGGAAATCAAAC
GC

SEQ ID NO: 4    DNVLTQSPAIMSASPGEKVTMTCSASSSVNYMYWYQQKPGSSPRLLIYDTSKLASGVPVRFSGSG
SGTSYSLTISRMEAEDAATYYCQQWSSSPLTFGVGAKLEIKR

IMGT            DNVLTQSPAIMSASPGEKVTMTCSASSSVNYMYWYQQKPGSSPRLLIYDTSKLASGVPVRFSGSGS
GTSYSLTISRMEAEDAATYYCQQWSSSPLTFGVGAKLEIKR

Chothia         DNVLTQSPAIMSASPGEKVTMTCSASSSVNYMYWYQQKPGSSPRLLIYDTSKLASGVPVRFSGSGS
GTSYSLTISRMEAEDAATYYCQQWSSSPLTFGVGAKLEIKR Kabat           DNVLTQSPAIMSASPGEKVTMTCSASSSVNYMYWYQQKPGSSPRLLIYDTSKLASGVPVRFSGSGS
GTSYSLTISRMEAEDAATYYCQQWSSSPLTFGVGAKLEIKR Honegger        DNVLTQSPAIMSASPGEKVTMTCSASSSVNYMYWYQQKPGSSPRLLIYDTSKLASGVPVRFSGSGS
GTSYSLTISRMEAEDAATYYCQQWSSSPLTFGVGAKLEIKR Bold faced: complementary determining regions

| Antibody A6 |
| --- |
| Heavy chain variable region |

SEQ ID NO: 5    CAGGTCCAACTGCAGCAGTCTGGGGCAGAGATTGTGAGGTCAGGGGCCTCAGTCAAGTTGTCC
TGCACAGCTTCTGGCTTCAGTATTACAGAATACTATATACACTGGGTGAAGCAGAGGCCTGATC
AGGGCCTGGAGTGGATAGGAATGATTGATCCTGAGAATGGTGATACTGACTATGCCCCGAAGT
TCCAGGGCAAGGCCACTATGACTGCAGACACATCGTCCAATACAGTCAACCTGCAACTCAGCAG
CCTGACATCTGAGGACACTGCCGTCTATTACTGTCATGGACCGGGCCCCCTTGAGTACTGGGGC
CAAGGCACCACTCTCACAGTCTCCTCG

SEQ ID NO: 6    QVQLQQSGAEIVRSGASVKLSCTASGFSITEYYIHWVKQRPDQGLEWIG**MIDPENGDTDYAPKFQ
GKATMTADTSSNTVNLQLSSLTSEDTAVYYCHGPGPLEY**WGQGTTLTVSS

IMGT            QVQLQQSGAEIVRSGASVKLSCTASGFSITEYYIHWVKQRPDQGLEWIGMIDPENGDTDYAPKFQG
KATMTADTSSNTVNLQLSSLTSEDTAVYYCHGPGPLEYWGQGTTLTVSS

Chothia         QVQLQQSGAEIVRSGASVKLSCTASGFSITEYYIHWVKQRPDQGLEWIGMIDPENGDTDYAPKFQ
GKATMTADTSSNTVNLQLSSLTSEDTAVYYCHGPGPLEYWGQGTTLTVSS Kabat           QVQLQQSGAEIVRSGASVKLSCTASGFSITEYYIHWVKQRPDQGLEWIGMIDPENGDTDYAPKFQG
KATMTADTSSNTVNLQLSSLTSEDTAVYYCHGPGPLEYWGQGTTLTVSS Honegger        QVQLQQSGAEIVRSGASVKLSCTASGFSITEYYIHWVKQRPDQGLEWIGM**IDPENGDTDYAPKFQ
GKATMTADTSSNTVNLQLSSLTSEDTAVYYCHGPGPLE**YWGQGTTLTVSS -continued

Antibody A6

Light chain variable region

| | |
|---|---|
| SEQ ID NO: 7 | GACATTGTAATGACCCAATCTCCACTCTCCCTGCCTGTCAGTCTTGGAGATCAAGCCTCCATCTC<br>TTGTAGATCTAGTCAGAGTATTGTACATAGTAATGGAAACACTTATTTAGAATGGTACCTGCAG<br>AAACCAGGCCAGTCTCCAAACCTCCTGATCTACAGAGTTTCCAACCGCTTTTCTGGGGTCCCAGA<br>CAGGTTCAATGGCAGTGGATCAGGGACAGATTTCACACTCAAGATCAGCAGAGTGGAGCCTGA<br>GGATCTGGGAGTTTATTCCTGCTTTCAAGCTTCACATGTTCCGTACACGTTCGGAGGGGGGACC<br>AAGCTGGAAATAAAACGC |
| SEQ ID NO: 8 | DIVMTQSPLSLPVSLGDQASISCRSSQSIVHSNGNTYLEWYLQKPGQSPNLLIYRVSNRFSGVPDRF<br>NGSGSGTDFTLKISRVEPEDLGVYSCFQASHVPYTFGGGTKLEIKR |
| IMGT | DIVMTQSPLSLPVSLGDQASISCRSSQSIVHSNGNTYLEWYLQKPGQSPNLLIYRVSNRFSGVPDRF<br>NGSGSGTDFTLKISRVEPEDLGVYSCFQASHVPYTFGGGTKLEIKR |
| Chothia | DIVMTQSPLSLPVSLGDQASISCRSSQSIVHSNGNTYLEWYLQKPGQSPNLLIYRVSNRFSGVPDRF<br>NGSGSGTDFTLKISRVEPEDLGVYSCFQASHVPYTFGGGTKLEIKR |
| Kabat | DIVMTQSPLSLPVSLGDQASISCRSSQSIVHSNGNTYLEWYLQKPGQSPNLLIYRVSNRFSGVPDRF<br>NGSGSGTDFTLKISRVEPEDLGVYSCFQASHVPYTFGGGTKLEIKR |
| Honegger | DIVMTQSPLSLPVSLGDQASISCRSSQSIVHSNGNTYLEWYLQKPGQSPNLLIYRVSNRFSGVPDRF<br>NGSGSGTDFTLKISRVEPEDLGVYSCFQASHVPYTFGGGTKLEIKR |

Bold faced: complementary determining regions

Antibody B1

Heavy chain variable region

| | |
|---|---|
| SEQ ID NO: 9 | CAGATTCAGCTTCAGGAGTCAGGACCTGGCCTCGTGAAACCTTCTCAGTCTCTGTCTCTCACCT<br>GCTCTGTCACTGGCTACTCAATAACCAGTGGTTATTATTGGAATTGGATCCGGCAGTTTCCAGG<br>AAATAAACTGGAATGGATGGGCTACATAAGTTACGACGGTACCAATAACTACAACCCATCTCT<br>CAAAGATCGAATCTCCATCACTCGTGACACATCTATGAACCAGTTTTTCCTGAAGTTGAATTCT<br>GTGACTACTGAGGACACAGCTACATATTACTGTTCAGTCTTATTAATACAGTACTTCAATATCT<br>GGGGCGCCGGAACCACGGTCACCGTCTCCTCG |
| SEQ ID NO: 10 | QIQLQESGPGLVKPSQSLSLTCSVTGYSITSGYYWNWIRQFPGNKLEWMGYISYDGTNNYNPSLK<br>DRISITRDTSMNQFFLKLNSVTTEDTATYYCSVLLIQYFNIWGAGTTVTSS |
| IMGT | QIQLQESGPGLVKPSQSLSLTCSVTGYSITSGYYWNWIRQFPGNKLEWMGYISYDGTNNYNPSLK<br>DRISITRDTSMNQFFLKLNSVTTEDTATYYCSVLLIQYFNIWGAGTTVTSS |
| Chothia | QIQLQESGPGLVKPSQSLSLTCSVTGYSITSGYYWNWIRQFPGNKLEWMGYISYDGTNNYNPSLK<br>DRISITRDTSMNQFFLKLNSVTTEDTATYYCSVLLIQYFNIWGAGTTVTSS |
| Kabat | QIQLQESGPGLVKPSQSLSLTCSVTGYSITSGYYWNWIRQFPGNKLEWMGYISYDGTNNYNPSLK<br>DRISITRDTSMNQFFLKLNSVTTEDTATYYCSVLLIQYFNIWGAGTTVTSS |
| Honegger | QIQLQESGPGLVKPSQSLSLTCSVTGYSITSGYYWNWIRQFPGNKLEWMGYISYDGTNNYNPSLK<br>DRISITRDTSMNQFFLKLNSVTTEDTATYYCSVLLIQYFNIWGAGTTVTSS |

Light chain variable region

| | |
|---|---|
| SEQ ID NO: 11 | GACATCCAGATGACACAGTCTCCAGCCTCCCTATCTGCATCTGTGGGAGAAACCGTCACCATCA<br>CATGTCGAACAAGTGAGAGTGTTAACAATTTCTTAGCCTGGTTTCACCAGAAACAGGGAAAT<br>CTCCTCAACTCCTGGTCTATCATGCAAAAACCTTAGCAGATGGTGTGTCATCAAGGTTCAGTGG<br>CAGTGGATCAGGAACACAATATTCTCTCAAGATCAACAGCCTGCAGCCTGAAGATTTTGGGAA<br>TTATTACTGTCAACATTTTTGGAGTATTCCGTGGACGTTCGGTGGAGGCACCAAGCTGGAAAT<br>CAAACGC |
| SEQ ID NO: 12 | DIQMTQSPASLSASVGETVTITCRTSESVNNFLAWFHQKQGKSPQLLVYHAKTLADGVSSRFSGS<br>GSGTQYSLKINSLQPEDFGNYYCQHFWSIPWTFGGGTKLEIKR |
| IMGT | DIQMTQSPASLSASVGETVTITCRTSESVNNFLAWFHQKQGKSPQLLVYHAKTLADGVSSRFSGS<br>GSGTQYSLKINSLQPEDFGNYYCQHFWSIPWTFGGGTKLEIKR |
| Chothia | DIQMTQSPASLSASVGETVTITCRTSESVNNFLAWFHQKQGKSPQLLVYHAKTLADGVSSRFSGS<br>GSGTQYSLKINSLQPEDFGNYYCQHFWSIPWTFGGGTKLEIKR |

-continued

Antibody B1

| | |
|---|---|
| Kabat | DIQMTQSPASLSASVGETVTITCRTSESVNNFLAWFHQKQGKSPQLLVYHAKTLADGVSSRFSGS GSGTQYSLKINSLQPEDFGNYYCQHFWSIPWTFGGGTKLEIKR |
| Honegger | DIQMTQSPASLSASVGETVTITCRTSESVNNFLAWFHQKQGKSPQLLVYHAKTLADGVSSRFSGS GSGTQYSLKINSLQPEDFGNYYCQHFWSIPWTFGGGTKLEIKR |

Bold faced: complementary determining regions

Antibody hB1

Heavy chain variable region

| | |
|---|---|
| SEQ ID NO: 13 | CAGATCCAGCTCCAAGAGAGCGGCCCCGGCCTGGTGAAGCCCAGCGAGAGCCTGAGCCTGAC CTGCTCGGTGACCGGCTACAGCATCACCAGCGGCTACTACTGGAACTGGATCAGGCAGTTCCC CGGCAACGGCCTGGAGTGGATGGGCTACATCAGCTACGACGGCACCAACAACTACAACCCCA GCCTGAAGGACAGGATCAGCATCACCAGGGACACCAGCAAGAACCAGTTCTTCCTGAAGCTG AACAGCGTGACCGCCGCCGACACCGCCACCTACTACTGCTCGGTGCTGCTGATCCAGTACTTC AACATCTGGGGCAAGGGCACCACCGTGACCGTGAGCAGC |
| SEQ ID NO: 14 | QIQLQESGPGLVKPSESLSLTCSVTGYSITSGYYWNWIRQFPGNGLEWMGYISYDGTNNYNPSLK DRISITRDTSKNQFFLKLNSVTAADTATYYCSVLLIQYFNIWGKGTTVTVSS |
| IMGT | QIQLQESGPGLVKPSESLSLTCSVTGYSITSGYYWNWIRQFPGNGLEWMGYISYDGTNNYNPSLKD RISITRDTSKNQFFLKLNSVTAADTATYYCSVLLIQYFNIWGKGTTVTVSS |
| Chothia | QIQLQESGPGLVKPSESLSLTCSVTGYSITSGYYWNWIRQFPGNGLEWMGYISYDGTNNYNPSLKD RISITRDTSKNQFFLKLNSVTAADTATYYCSVLLIQYFNIWGKGTTVTVSS |
| Kabat | QIQLQESGPGLVKPSESLSLTCSVTGYSITSGYYWNWIRQFPGNGLEWMGYISYDGTNNYNPSLK DRISITRDTSKNQFFLKLNSVTAADTATYYCSVLLIQYFNIWGKGTTVTVSS |
| Honegger | QIQLQESGPGLVKPSESLSLTCSVTGYSITSGYYWNWIRQFPGNGLEWMGYISYDGTNNYNPSLK DRISITRDTSKNQFFLKLNSVTAADTATYYCSVLLIQYFNIWGKGTTVTVSS |

Light chain variable region

| | |
|---|---|
| SEQ ID NO: 15 | GACATCCAGATGACCCAGAGCCCCAGCAGCCTGAGCGCCAGCGTGGGCGAGAGGGTGACCA TCACCTGCCGTACCAGCGAGAGCGTGAACAACTTCCTGGCCTGGTTCCACCAGAAGCCCGGCA AGAGCCCCAAGCTGCTGGTGTACCACGCCAAGACCCTGGCCGACGGCGTGAGCAGCAGGTTC AGCGGCAGCGGCAGCGGCACCCAGTACAGCCTGAAGATCAACAGCCTGCAACCCGAGGACTT CGGCAACTACTACTGCCAGCACTTCTGGAGCATCCCCTGGACCTTCGGCGGCGGCACCAAGCT GGAGATCAAGAGG |
| SEQ ID NO: 16 | DIQMTQSPSSLSASVGERVTITCRTSESVNNFLAWFHQKPGKSPKLLVYHAKTLADGVSSRFSGSG SGTQYSLKINSLQPEDFGNYYCQHFWSIPWTFGGGTKLEIKR |
| IMGT | DIQMTQSPSSLSASVGERVTITCRTSESVNNFLAWFHQKPGKSPKLLVYHAKTLADGVSSRFSGSG SGTQYSLKINSLQPEDFGNYYCQHFWSIPWTFGGGTKLEIKR |
| Chothia | DIQMTQSPSSLSASVGERVTITCRTSESVNNFLAWFHQKPGKSPKLLVYHAKTLADGVSSRFSGSG SGTQYSLKINSLQPEDFGNYYCQHFWSIPWTFGGGTKLEIKR |
| Kabat | DIQMTQSPSSLSASVGERVTITCRTSESVNNFLAWFHQKPGKSPKLLVYHAKTLADGVSSRFSGSG SGTQYSLKINSLQPEDFGNYYCQHFWSIPWTFGGGTKLEIKR |
| Honegger | DIQMTQSPSSLSASVGERVTITCRTSESVNNFLAWFHQKPGKSPKLLVYHAKTLADGVSSRFSGSG SGTQYSLKINSLQPEDFGNYYCQHFWSIPWTFGGGTKLEIKR |

Bold faced: complementary determining regions

An anti-RSPO3 antibody disclosed herein includes heavy chain complementary determining regions CDR1, CDR2, and CDR3 from a heavy chain variable region sequence selected from SEQ ID NOs: 2, 6, 10, and 14, and light chain complementary determining regions CDR1, CDR2, and CDR3 from a light chain variable region sequence selected from SEQ ID NOs: 4, 8, 12, and 16. The three CDRs in each of the regions are shown above. A skilled practitioner would be able to identify the CDRs using various methods known in the art.

The antibody can bind specifically to RSPO3, i.e., binds to RSPO3 with a higher affinity than other non-RSPO3 proteins, and may disrupt the interaction between RSPO3 and its ligands. The RSPO3 proteins the antibody can bind include a human RSPO3 (e.g., GenBank accession no. NP_116173), a mouse RSPO3, or other mammalian homologs. In some embodiments, the antibody binds to the same epitope as antibody A4, A6, B1, or hB1.

The term "antibody" as used herein includes various antibody structures that have an antigen-binding activity, including but not limited to, monoclonal antibodies, polyclonal antibodies, full-length antibodies or fragments thereof, antibodies that contain an Fc region, Fab fragments, Fab' fragments, F(ab')$_2$ fragments, single-chain antibodies, scFV multimers, monovalent antibodies, multivalent antibodies, humanized antibodies and chimeric antibodies.

Based on the antibody sequences disclosed herein and their CDRs, a skilled practitioner would be able to produce an anti-RSPO3 antibody in various forms using methods described herein or known in the art, e.g., recombinant methods.

Also contemplated herein is an isolated nucleic acid molecule (e.g., an expression vector) that includes a nucleic acid sequence encoding the anti-RSPO3 antibody described herein or a component thereof. For example, the nucleic acid sequence can encode SEQ ID NO: 2, 4, 6, 8, 10, 12, 14, or 16, or a polypeptide that contains one or more CDRs from these sequences. A host cell containing the nucleic acid molecule is also provided herein. The nucleic acid molecule and host cell can be used to generate the anti-RSPO3 antibody.

Any of the antibodies described herein can be used to inhibit binding between RSPO3 and its ligands, inhibit an RSPO3 function, detect an RSPO3 protein or a fragment thereof in a sample (e.g., in an immunoassay), bind to a tissue or cell that expresses RSPO3 (e.g., to identify a cell or to isolate an RSPO3-expressing cell), inhibit the growth or metastasis of a cancer cell, treat a cancer in a subject, or generate an anti-RSPO3 antibody variant.

The term "sample" can refer to any biological sample, e.g., a bodily fluid sample, a blood sample, a cell sample, a urine sample, a saliva sample, or a tissue sample.

Any of the anti-RSPO3 antibodies described herein can be formulated as a pharmaceutical composition suitable for various routes of administration, e.g., intravenous, intraarticular, conjunctival, intracranial, intraperitoneal, intrapleural, intramuscular, intrathecal, or subcutaneous route of administration. The pharmaceutical composition can be an aqueous solution or lyophilized formulation. It can contain a pharmaceutically acceptable carrier, e.g., a buffer, excipient, stabilizer, or preservative. The pharmaceutical composition can include other active ingredients that work together with the anti-RSPO3 antibody, e.g., another therapeutic agent. The pharmaceutical composition can be used to treat a cancer or tumor in a subject.

The anti-RSPO3 antibodies can also be conjugated to another molecule or moiety, e.g., a protein or peptide, a drug (e.g., a cytotoxic drug), a detectable label (e.g., fluorescent label), or a solid support (e.g., a bead or a plate). Such antibody conjugates can be used for various purposes such as treating cancers or detecting RSPO3 in samples.

Cancers or tumors that can be treated with any of the anti-RSPO3 antibodies include, but are not limited to, colon cancer, leukemia, colorectal cancer, ovarian cancer, pancreatic cancer, lung cancer, liver cancer, breast cancer, kidney cancer, prostate cancer, gastrointestinal cancer, melanoma, cervical cancer, bladder cancer, glioblastoma, and head and neck cancer. The treatment can be performed alone or in conjunction with other drugs or therapies. In some embodiments, the cancer or tumor has a higher expression level of RSPO3 as compared to a control (e.g., another cancer, a normal tissue, or a normal cell), or carries an RSPO-fused gene or an RSPO3 translocation. In some embodiments, the cancer or tumor has an adenomatous polyposis coli (APC) mutation, a β-catenin mutation, or hyperactivated Wnt signaling. Optionally, before administering the anti-RSPO3 antibody to a subject, it can be determined, using methods known in the art, whether the cancer or tumor in the subject exhibits a higher expression level of RSPO3, or has an RSPO-fused gene or an RSPO3 translocation, an APC mutation, a β-catenin mutation, or hyperactivated Wnt signaling.

A "subject" refers to a human or a non-human animal. "Treating" or "treatment" refers to administration of a compound or composition to a subject, who has a disorder, with the purpose to cure, alleviate, relieve, remedy, delay the onset of, or ameliorate the disorder, the symptom of the disorder, the disease state secondary to the disorder, or the predisposition toward the disorder. An "effective amount" refers to an amount of the compound or composition that is capable of producing a medically desirable result in a treated subject.

The anti-RSPO3 antibody described herein may be modified to produce an anti-RSPO3 antibody with a desired property, e.g., improved stability, binding specificity, or in vivo efficacy. An antibody variant can be prepared by introducing one or more modifications into the nucleotide sequence encoding the antibody, or by peptide synthesis. The modifications can be introduced into one or more of the CDRs, or at a site outside of the CDRs. The modifications can include, for example, deletions, insertions and/or substitutions. Methods known in the art can be used to generate antibody variants. The modifications may be introduced randomly or site-specifically. The alanine scanning mutagenesis technique can be used to identify residues that can be modified without abolishing the antigen binding activity and specificity of an antibody.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are herein incorporated by reference in their entirety.

Example 1

Materials and Methods

1. Cell Lines

Cell lines were purchased from the ATCC with the exception of ExpiCHO-S cells, which were obtained from Thermo Fisher Scientific. DLD-1 and NCI-H2030 cell lines were grown in RPMI supplemented with 10% FBS, 293T cell line in DMEM with 10% FBS, and ExpiCHO-S in ExpiCHO™ Expression Medium Medium (Thermo). Human SNU-1411 colon tumor cells were obtained from Korean cell line bank and cultured in RPMI medium supplemented with 10% FBS (v/v) and penicillin (100 U/ml)/streptomycin (100 μg/ml). Cultures were maintained in a humidified incubator at 37° C. in 5% $CO_2$/95% air.

2. Reporter Assays

Wnt signaling leads to β-catenin/TCF dependent transcriptional responses. MDA-MB436-TCF/LEF-Luc cells, a gift from Dr. Kelvin Kun-Chih Tsai, were employed to monitor the activity of Wnt signal transduction pathways. See, e.g., Wang et al. (2013). Gastroenterology (145): 1110-1120. In brief, MDA-MB436-TCF/LEF-Luc cells were seeded in black flat bottom 96 well culture plates (Costar) in RSPO Medium supplemented with 10% FBS and incubated overnight at 37° C., 5% $CO_2$. 24 hours after incubation, cells were treated with anti-RSPO3 ab, 20 ng/ml WNT3a (R&D system) and RSPO ligands (Peprotech Systems) where appropriate and further incubated for 16 hours. Luciferase activity was measured using Bright-Glo Luciferase Assay System (Promega).

3. Hybridoma Generation and RSPO3 Antibodies Purification

Mouse monoclonal antibody against RSPO3 was generated by LTK BioLaboratories (Taiwan). Briefly, approximately 0.5-1.5 mg of RSPO3 was used for immunization in mice. Hybridoma cells were then generated by fusing immune spleen cells with myeloma cell, and 11 hybridoma clones were isolated. Hybridomas were cultured in 96-well tissue culture plates with IMDM (GIBCO) and inactivated 20% FBS. The cell supernatants were then screened for binding capability to RSPO3 using standard ELISA and Western blotting as described below to select positive clones. Cells from positive clones were subcloned to 96-well plates, and single clones were recovered and gradually adapted to growth in serum free medium (SFM, HyClone) supplemented with inactivated 20% FBS. See FIG. 1. The hybridoma cells were injected intraperitoneally into these mice to induce formation of ascites tumors and production of ascitic fluid. Ascitic fluid was loaded onto protein A-Sepharose according to the standard protocol. Purified RSPO3 Ab was dialyzed against azide free PBS buffer.

4. Sequencing and Cloning of RSPO3 Antibodies from Hybridomas

To determine the cDNA sequence of IgG heavy and light chains in the hybridomas, total RNA was isolated from hybridoma cells and cDNA was prepared with reverse transcriptase by random hexamers. The mouse Ig-Primer Set (Novagen, 69831-3) and Ig-Primer mix (shown in Table 1) were used for PCR amplification for variable domain determination. The PCR products were cloned into pJET1.2/blunt cloning vector (CloneJET PCR cloning Kit, Thermo) for DNA sequence analysis. The corresponding genetic codes and encoding amino acid sequences of RSPO3 antibodies are disclosed above.

TABLE 1

Primer sets for cloning the RSPO3 Ab Variable regions

Primers VL-for

| | |
|---|---|
| VL-for k1 | GACAWTGTTCTCACCCAGTC (SEQ ID NO: 17) |
| VL-for k2 | GACATCCAGATGACACAGWC (SEQ ID NO: 18) |
| VL-for k3 | GATRTTGTGATGACCCAGWC (SEQ ID NO: 19) |
| VL-for k4 | GACATTSTGMTGACCCAGTC (SEQ ID NO: 20) |
| VL-for k5 | GATGTTGTGVTGACCCAAAC (SEQ ID NO: 21) |
| VL-for k6 | GACACAACTGTGACCCAGTC (SEQ ID NO: 22) |
| VL-for k7 | GAYATTKTGCTCACTCAGTC (SEQ ID NO: 23) |
| VL-for k8 | GATATTGTGATRACCCAGGM (SEQ ID NO: 24) |
| VL-for k9 | GACATTGTAATGACCCAATC (SEQ ID NO: 25) |
| VL-for k10 | GACATTGTGATGWCACAGTC (SEQ ID NO: 26) |
| VL-for k11 | GATRTCCAGATGAMCCAGTC (SEQ ID NO: 27) |
| VL-for k12 | GATGGAGAAACAACACAGGC (SEQ ID NO: 28) |

TABLE 1-continued

Primer sets for cloning the RSPO3 Ab Variable regions

| | |
|---|---|
| VL-for λ1 | GACGCTGTTGTGACTCAGGA (SEQ ID NO: 29) |
| VL-for λ2 | GACCYTGTGCTCACTCAGTC (SEQ ID NO: 30) |

Primers VL-rev

| | |
|---|---|
| VL-rev 1 | GCGTTTBATTTCCAGCTTGG (SEQ ID NO: 31) |
| VL-rev 2 | GCGTTTTATTTCCAATTTTG (SEQ ID NO: 32) |
| VL-rev λ | GCCTAGGACAGTCAMCYTG (SEQ ID NO: 33) |

Primers VH-for

| | |
|---|---|
| VH-for 1 | GAGGTTCDSCTGCAACAGTY (SEQ ID NO: 34) |
| VH-for 2 | CAGGTGCAAMTGMAGSAGTC (SEQ ID NO: 35) |
| VH-for 3 | GAVGTGMWGCTGGTGGAGTC (SEQ ID NO: 36) |
| VH-for 4 | CAGGTTAYTCTGAAAGAGTC (SEQ ID NO: 37) |
| VH-for 5 | GAKGTGCAGCTTCAGSAGTC (SEQ ID NO: 38) |
| VH-for 6 | CAGATCCAGTTSGYGCAGTC (SEQ ID NO: 39) |
| VH-for 7 | CAGRTCCAACTGCAGCAGYC (SEQ ID NO: 40) |
| VH-for 8 | GAGGTGMAGCTASTTGAGWC (SEQ ID NO: 41) |
| VH-for 9 | GAAGTGAAGMTTGAGGAGTC (SEQ ID NO: 42) |
| VH-for 10 | GATGTGAACCTGGAAGTGTC (SEQ ID NO: 43) |
| VH-for 11 | CAGATKCAGCTTMAGGAGTC (SEQ ID NO: 44) |
| VH-for 12 | CAGGCTTATCTGCAGCAGTC (SEQ ID NO: 45) |
| VH-for 13 | CAGGTTCACCTACAACAGTC (SEQ ID NO: 46) |
| VH-for 14 | CAGGTGCAGCTTGTAGAGAC (SEQ ID NO: 47) |
| VH-for 15 | GARGTGMAGCTGKTGGAGAC (SEQ ID NO: 48) |

Primers VH-rev

| | |
|---|---|
| VH-rev 1 | CGAGGAGACGGTGACMGTGG (SEQ ID NO: 49) |
| VH-rev 2 | CGCAGAGACAGTGACCAGAG (SEQ ID NO: 50) |
| VH-rev 3 | CGAGGAGACTGTGAGASTGG (SEQ ID NO: 51) |

R = A or G; Y = C or T; M = A or C; K = G or T; S = C or G; W = A or T; H = A or C or T; B = C or G or T; V = A or C or G; D = A or G or T).

5. Construction, Expression and Purification of B1, hB1 and the Reference Antibody 131R010 from ExpiCHO-S Cells The cDNA sequences of the VH and VL regions from antibodies producing hybridomas were synthesized by GeneDireX, Inc. pFUSEss-CHIg-hG1e1 and pFUSE2ss-CLIg-hk (InvivoGen) were introduced the synthesized variable region before the constant regions of the heavy (CH) and light (CL) chains, respectively. For pFUSEss-CHIg-hG1e1 cloning, the variable region of heavy chain was inserted by EcoRI and Nhe I cutting site under the hIL2 signal sequence to make the amino acid sequence in frame. Respectively, the variable region of light chain was inserted into pFUSE2ss-CLIg-hk by EcoRI and BsiWI. To use pcDNA3.4 (Invitogen) as antibody expression vector, the full length antibodies of heavy chain and light chain were amplified using hIgHG-F/hIgHG-R and CLIg-F/CLIg-R primers from previous constructed pFUSEss plasmid then following the TA TOPO cloning described as standard protocol (Thermo).

```
hIgHG-F;
                                      (SEQ ID NO: 52)
5'-CATGCCTAGGCCACCATGTACAGGATGCAACTCCTGTC-3' hIgHG-R:
                                      (SEQ ID NO: 53)
5'-GGGTTTCATATGTCATTTACCCGGAGACAGG-3'

CLIg-F:
                                      (SEQ ID NO: 54)
5'-GGAAGATATCCCACCATGTACAGGATGCAACTCCTGTC-3'

CLIg-R:
                                      (SEQ ID NO: 55)
5'-CCTTAATTAACTAACACTCTCCCCTGTTGAAGC-3'
```

For recombinant antibodies production, ExpiCHO-S™ cells were co-transfected with the recombinant plasmids pcDNA3.4 encoding the heavy chain and light chain (ex. pcDNA3.4-hB1H and pcDNA3.4-hB1L) by the ratio of 2:3. The ExpiCHO™ expression medium was harvest after 8-10 days using the standard protocol. The resulting antibody was purified from the supernatant using Mabselect SuRe™ XL (GE Healthcare) affinity chromatography.

6. Reactivity of Hybridoma Antibodies on RSPO3-Binding

To assess the RSPO-binding capability of antibodies, purified antibodies were reacted with RSPO1, 2, 3, and 4 on immunoblots. To perform antigen-binding ELISA assay, 96-well high binding polystyrene plates (Corning) were coated with 2 μg/ml of recombinant RSPO3 preparation in the capture buffer by overnight incubation at 4° C. Coated plates were washed twice with PBS supplemented with 0.05% Tween 20 (PBST). The plates were blocked with PBST—10% BSA and assayed with ELISA standard protocol for 1 h at room temperature.

7. Antibody Isotyping

For antibody isotyping, microtiter plates were coated with RSPO3 as described above, and then assayed with the Mouse MonoAb ID Kit (HRP) from Zymed Laboratories in accordance with the manufacturer's instructions.

8. Antibody Engineering: Ab Humanization

To generate humanized and fully functional RSPO3 antibodies, antibody humanization technology was used in this study and the service was provided by Industrial Technology Research Institute (ITRI) (Hsiuchu, Taiwan). The humanized antibody with ideal amino acid sequence is shown above. However, the antibody resurfacing method usually exhibits little change in affinity and stability. See, e.g., Roguska et al. (1996). Protein Eng (9): 895-904; and Roguska et al. (1994). Proc Natl Acad Sci USA (91): 969-973.

9. Binding Screening of RSPO3 Ab

The streptavidin-coated sensors were coated with 10 μg/ml of biotinylated RSPO3 as described in the handbook of ForteBio. Antibody concentrations were in the range of 0.75 and 93.8 nM. Quantitative kinetic binding analysis was performed with pH-adjusted PBS with 0.5% BSA. All steps were run at 30° C. with a continuous shaking speed at 1000 rpm.

10. Binding Analysis of RSPO3 Ab

The binding kinetics between α-RSPO3 Abs and recombinant human RSPO3 protein (hRSPO3) were performed at 25° C. using a Biacore T200 biosensor equipped with a CM5 Series S Sensor Chip (GE Healthcare). Running buffer was HBS-EP Buffer (0.01 M HEPES pH 7.4, 0.15 M NaCl, 3 mM EDTA, 0.005% v/v Surfactant P20) with final pH 7.4. hRSPO3 protein was immobilized on CM5 sensor chips with coating densities of about 27.5 response units (RU). The α-RSPO3 Abs were serially diluted 2-fold from 6.25 nM to 0.39 nM in HBS-EP and were injected over the chip surface for 120 s each at a flow rate of 30 μL/min, followed by a final 900 s dissociation phase. Obtained sensorgrams were corrected by double subtracting the signal obtained on a reference surface and the signal of the running buffer. Sensorgrams were fit globally with BIAcore T200 evaluation software 3.0 using 1:1 binding model to yield affinity constants (KD values) for α-RSPO3 Abs. Replicate measurements were made in separate experiments, using independently prepared α-RSPO3 Abs dilution series and huRSPO3-coated chip surfaces.

11. Antibody Binding Epitope Mapping in PepSet ELISA

ELISA for PepSet library was employed to determine α-RSPO3 hB1 antibodies and RSPO3 binding epitope. The deduced amino acid sequence of RSPO3 (GenBank accession no. NP_116173) was used as the reference sequence to design the PepSet library of biotinylated linear peptides that cover the mature domain of RSPO3. The 121 peptides synthesized by Mimotopes (Victoria, Australia) were 10 amino acids in length and offset by 2 residues in these two formats: Biotin-SGSG-PEPTIDE-NH2 for N-terminal peptide and Biotin-SGSG-PEPTIDE-OH for the C-terminal peptide. The peptides (1-3 mg) were dissolved in 200 microliter 80/20 DMSO/water mixture and further diluted at 1:200 in PBS containing 0.1% BSA and 0.1% sodium azide as working solution. In order to attach different biotinylated peptides on each well of the plates, plates coated with NeutrAvidin and blocked with BSA (Thermo Scientific Pierce, Rockford, Ill.) were utilized. Plates were washed three times with 1× PBS with 0.1% Tween 20 and then 100 ml biotinylated peptide solution was applied to each well of plates. After one hour incubation at room temperature, plates were washed three times again with 1× PBST. α-RSPO3 antibodies at 10 μg/ml were then added to each well of plates and the plates were incubated with agitation for one hour. Plates were washed three times again to remove antibodies which did not bind to peptides. To detect bound anti-RSPO3 antibodies, Goat anti-human IgG-Fc-HPR was then applied to plates for one hour. After removing extra detection antibodies by washing the plates with 1×PBST, 100 μl Tetramethylbenzidine (TMB) substrate solution was added to each well for 20 minutes. The colorimetric reaction were then stop by 2N HCL and the optical density at 450 nm of each well were determined immediately.

12. Antibody Binding Epitope Mapping Using Synthetic Cyclic Peptides with Intrachain Disulfide Bond In order to attach different biotinylated peptides or proteins on the plates, the biotinylated cyclic peptides, at 1 μg/ml, and biotinylated recombinant human RSPO3, at 100 ng/ml, were applied to NeutrAvidin pre-coated plates (Thermo Scientific Pierce). Cyclic peptides were treated with 0.1M DTT first to generate reducing form of cyclic peptides. To examine the binding between hB1 and different cyclic peptides, hB1, at 2 μg/ml, was added to each well of the plates. After incubation and washing, goat anti-human IgG-Fc-HPR (Chemicon) was then applied to plates. After removing extra detection antibodies by washing the plates with 1×PBST, 100 μl Tetramethylbenzidine (TMB) substrate solution was added to each well for 10 minutes. The colorimetric reaction was then stopped by 2N HCL and the optical density at 450 nm of each well was determined immediately.

13. Competitive ELISA of Ab/Receptor/Ligand Binding

To exam whether different α-RSPO3 antibodies competed with LGR5 or RNF43 to the binding of RSPO3, recombinant human RSPO3 (Peprotech) 500 ng/ml was coated on plates. Recombinant LGR5 (22-560)-Fc (R&D) was conjugated with biotin for detection purpose. Then biotinylated LGR5, at 30 ng/ml, was respectively mixed with various concentrations of either α-RSPO3 antibodies or an isotype control antibody and applied to RSPO3 coated wells. An anti-streptavidin-HRP antibody was then added to detect bound biotinylated LGR5. Recombinant human RSPO3 (Peprotech) at 500 ng/ml was coated on the plates.

To exam whether different α-RSPO3 antibodies might compete with the binding of RSPO3 to RNF43, mixtures of recombinant Hig-tagged RNF43 (RNF43-His16108-H08H, Sino Biological) at 200 ng/ml and 20 µg/ml of different α-RSPO3 antibodies, respectively, were applied to each well. Mouse anti-His tag antibody-HRP (BioLegend) was then added for detection of bound RNF43-His. After incubation, excess detection antibody was removed by washing the plates with 1×PBST, 100 µl Tetramethylbenzidine (TMB), followed by addition of the substrate solution to each well. The colorimetric reaction was then stopped by 2N HCL and the optical density at 450 nm of each well were determined immediately.

14. Effect of α-RSPO3 Abs in "Wound Healing" Capacity of Human Colorectal Adenocarcinoma DLD1 Cells DLD-1 cells were seeded at 40000 cells per well in Culture-Insert 2 Well (ibidi, Martinsried, Germany) with RPMI medium containing 10% FBS for 16 hours. After removing the culture insert, cells were either treated with 100 µg/ml control human IgG1 antibodies or 100 µg/ml anti-RSPO3 antibodies in low serum (0.5%) medium in the presence of 20 ng/ml Wnt3a and 50 ng/ml RSPO3. Samples were then subjected to live cell image time lapse microscopy system (Leica AF6000 LX) to observe migration of DLD-1 cells. Three positions of each well under 10× objective lens were selected at the beginning and phase images of these positions were acquired by Zyla 4.2 sCMOS camera every 30 minutes for up to 60 hours.

15. Evaluation of Efficacy of hB1 in CR3150 RSPOhigh PDX Models

To evaluate preclinical in vivo efficacy, colorectal cancer patient-derived xenograft (PDX) model CR3150 was used in this study and the service was provided by Crown Bioscience Inc. (Taicang, China). Female BALB/c nude mice were inoculated subcutaneously at the right flank with one fragment of primary CR3150 tumor (2-3 mm in diameter) for tumor development. When the average tumor size reached about 190 mm$^3$, tumor-bearing mice were randomly allocated into groups and 25 mg/kg of the test articles or vehicle (PBS) were injected intraperitoneally (i.p.) twice a week for 4.5 weeks. Tumor volume was measured by caliper twice weekly and using the formula: TV=0.5×a×b$^2$, where a and b are the long and short diameters of the tumor, respectively. Animals were sacrificed due to tumor size reaching humane endpoints, and the last value of the tumor volume was carried forward until the end of the study.

Statistical analyses including the mean and standard error were provided for the tumor volume. Since the two treatment regimens were independent, for comparison between each treatment against the control, an independent sample t-test was performed. All data was analyzed using SPSS 18.0. P<0.05 was considered to be statistically significant.

16. Evaluation of Molecular Responses of hB1 in CR3150 PDX Models

Tumor samples from RSPO3 Fusion PDX model were analyzed by Q-PCR. RNA was extracted by TRIzol regent (Invitrogen, #15596-018) and the cDNA was synthesized by M-MLV RT, RNase H Minus (Promega, #M3682). The copy number of antibodies-treated human tumors grown in murine xenografts was determined using real-time quantitative RT-PCR (KAPA SYBR FAST qPCR Kit, KAPABIOSYSTEMS, #KK4604). 2 µl cDNA was add to 18 µl PCR mixture and the reaction was started by initiating step of 1 min at 95° C., followed by 40 cycles of amplification including 2 s at 95° C. and 30 sec at 60° C. The real-time PCR reaction and data analyses were performed with LightCycler 1.0 system (Roche). GAPDH was used as housekeeping gene for normalization. The primers sets used for the PCR analysis are in Table 2.

TABLE 2

| Primer sets used for Q-PCR analyses | |
|---|---|
| GAPDH-F | GAAGGTGAAGGTCGGAGTC (SEQ ID NO: 56) |
| GAPDH-R | GAAGATGGTGATGGGATTTC (SEQ ID NO: 57) |
| LGR5-F | TGATGACCATTGCCTACAC (SEQ ID NO: 58) |
| LGR5-R | GTAAGGTTTATTAAAGAGGAGAAG (SEQ ID NO: 59) |
| AXIN2-F | TCCCCACCTTGAATGAAGAA (SEQ ID NO: 60) |
| AXIN2-R | TGGTGGCTGGTGCAAAGA (SEQ ID NO: 61) |
| TCF7-F | CACCCGGCCATTGTGC (SEQ ID NO: 62) |
| TCF7-R | GCTTTTCCCTCGACCGC (SEQ ID NO: 63) |
| CD133F | GCATTGGCATCTTCTATGGTT (SEQ ID NO: 64) |
| CD133-R | CGCCTTGTCCTTGGTAGTGT (SEQ ID NO: 65) |
| CD44-F | TCCAACACCTCCCAGTATGACA (SEQ ID NO: 66) |
| CD44-R | TCTTCAGGATTCGTTCTGTATT (SEQ ID NO: 67) |
| CEACAM7-F | GCCAAACAGTGCCCAGACC (SEQ ID NO: 68) |
| CEACAM7-R | CTCTCGACCGTTGTGTGCG (SEQ ID NO: 69) |
| KRT20-F | ACGCCAGAACAACGAATACC (SEQ ID NO: 70) |
| KRT20-R | ACGACCTTGCCATCCACTAC (SEQ ID NO: 71) |

17. Evaluation of Efficacy of hB1 in RSPO$^{high}$ NCI-H2030 Lung Cancer Cell-Derived Xenograft (CDX) Models To evaluate the preclinical in vivo efficacy, RSPO$^{high}$ NCI-H2030 lung cancer cell-derived xenograft (CDX) model was used in this study. Female nude mice were inoculated subcutaneously at the right flank with one fragment of NCI-H2030 (5*10$^6$) for tumor development. When the average tumor size reached about 250 mm$^3$, tumor-bearing mice were randomly allocated into groups and 25 mg/kg of the test articles, 50 mg/kg of carboplatin or vehicle (isotype IgG) were injected intravenously (i.v.) every week for 4 weeks. Tumor volume was measured by caliper every three days (one day dosing and 2 days off) and using the formula: TV=0.5×a×b$^2$, where a and b is the long and short diameters of the tumor, respectively. Animals were sacrificed due to tumor size reaching humane endpoints, and the last value of the tumor volume was carried forward until the end of the study.

Statistical analyses were including the mean and standard error, are provided for the tumor volume. Since the two treatment regimens were independent, for comparison between each treatment against control, an independent sample was performed. All data was analyzed using 2way ANOVA multiple comparisons by Prism. $P<0.05$ was considered to be statistically significant.

18. Effect of Anti-RSPO3 Antibody in Combination with Carboplatin on Growth of SNU-1411 Colon Xenograft Tumors Carrying PTPRK(e13)-RSPO3(e2) Fusion Transcript To determine the effect of antibodies on SNU-1411 xenograft tumor, tumor-bearing animals were randomized and treatment began when mean tumor volumes reached approximately 150-200 mm$^3$. Antibodies were given once every other week (Q2W) and paclitaxel was administered once a week (Q1W). Both antibody and paclitaxel were administered intravenously. Tumor growth was measured twice a week by an electronic caliper. Tumor volumes were calculated with the formula $(L \times W^2)/2$, where L was the longest and W was the shortest axis of the tumor. Animal weights were recorded once a week. Mice were examined frequently for overt signs of any adverse drug-related side effects. At the end of the study, all the mice were euthanized.

19. Statistical Analysis

Data were expressed as mean±S.E.M. Differences in mean values between groups were analyzed by non-parametric t test. Multiple comparisons used a one-way ANOVA test follow by Tukey's post-test comparison. Differences of $p<0.05$ were considered significantly different. Software for statistical analysis was by GraphPad Prism4 (GraphPad Software Inc).

20. Tissue Microarray (TMA)-Based Immunohistochemistry Method

IHC labeling intensity for RSPO3 protein in tissue slides by hB1 was scored and analyzed. All tissue microarray slides were obtained from US Biomax. Pancreatic adenocarcinoma tissue microarray slide (PA807), containing 35 cases of adenocarcinoma, 1 each of carcinoid, acinic cell carcinoma, adenosquamous carcinoma, islet cell tumor and squamous cell carcinoma, 27 cancer adjacent pancreatic tissue, and 13 normal pancreatic tissue, single core per case, was stained for RSPO3 by hB1 (1:100). The non-small cell lung carcinoma (NSCLC) tissue microarray slide (LC10012b), containing 45 cases of NSCLC with matched cancer adjacent lung tissue (26 squamous cell carcinoma, 18 adenocarcinoma and 1 adenosquamous carcinoma) and 5 normal lung tissues, duplicate cores per case, was stained for levels of RSPO3 by hB1 (1:100). The breast invasive ductal carcinoma tissue microarray slide (BR1505c), containing 75 cases of breast invasive ductal carcinoma, duplicate cores per case, was stained for RSPO3 by hB1 (1:100). The colorectal carcinoma and matched adjacent normal tissue microarray slide (CO10012b) with lymph node metastasis carcinoma, containing 36 cases of colorectal adenocarcinoma and matched adjacent normal tissue, 9 each of lymph node metastasis carcinoma and normal lymph node tissue, plus 10 normal colorectum tissue, was stained for RSPO3 by hB1 (1:40).

The signal intensities of the slides were evaluated by two board-certified pathologists. Immunostaining score (range: 0, 2-8) was defined as proportion score+intensity score in accordance with a previous report (proportion score: 0=0/100, 1=1/100~1/10, 2=1/10~1/3, 3=1/3~2/3, 4=2/3~1, and 5=100/100; intensity score: 0=negative, 1=weak, 2=intermediate, and 3=strong).

Example 2

Reactivity of α-RSPO3 Hybridoma Antibodies on RSPO1-4 Binding

Figure 2A:
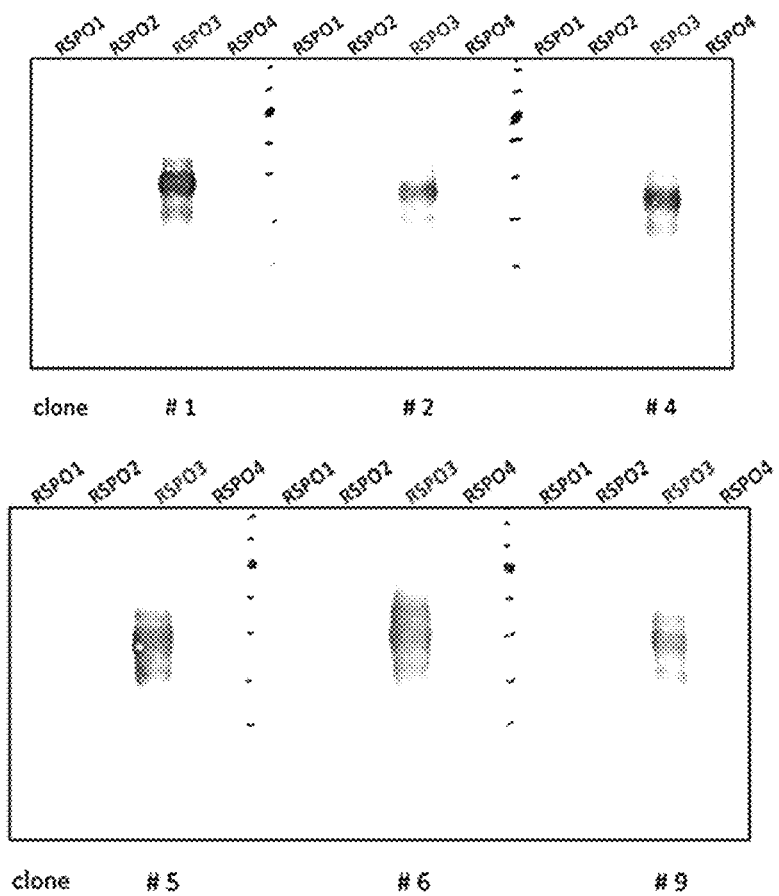
FIG. 2 is a set of Western blots showing Anti-RSPO3 hybridoma antibodies reactivity. These hybridoma antibodies were reacted with RSPO1-4 antigen immunoblots The M.W. of markers are indicated. (A) A1, A2, A4, A5, A6, and A9 clones; and (B) B1, B3, B4, B8, and B9 clones.
Figure 2B:
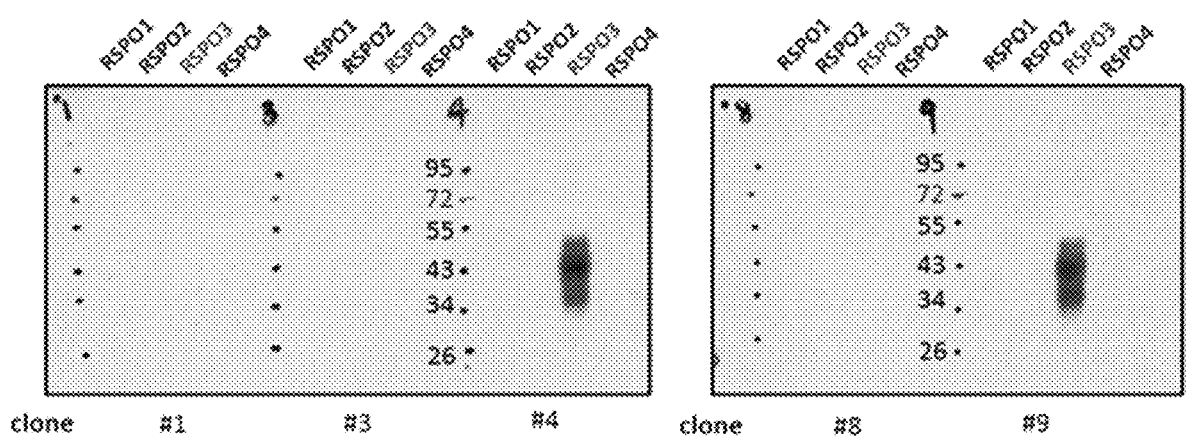
Figure 3A:
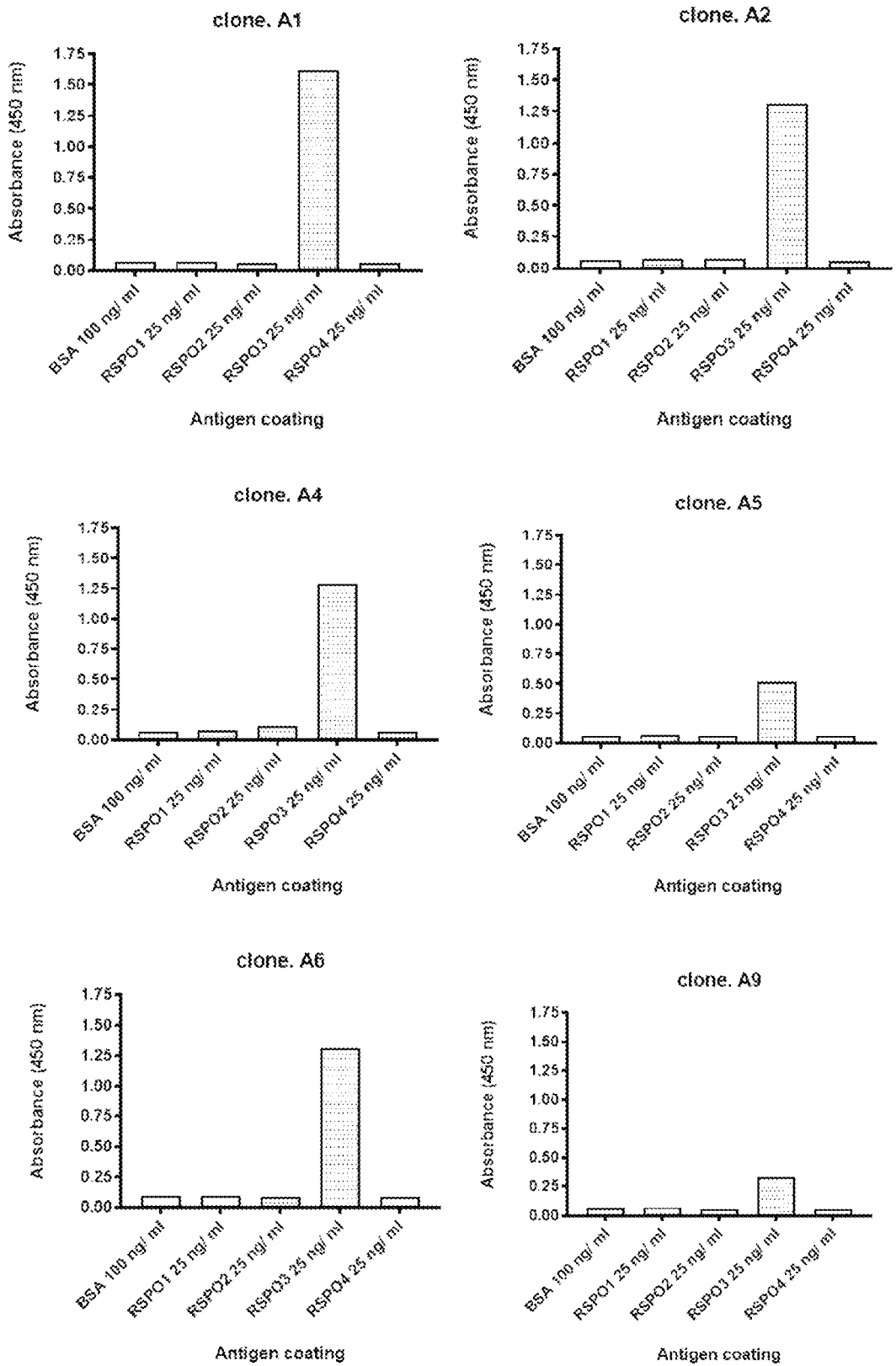
FIG. 3 is a set of graphs showing Anti-RSPO3 hybridoma antibodies reactivity measured by ELISA. These hybridoma antibodies were reacted with RSPO1-4 antigen immunoblots, which reflect with the RSPO3 antigen. (A) A1, A2, A4, A5, A6, and A9 clones; and (B) B1, B3, B4, B8, and B9 clones.
Figure 3B:
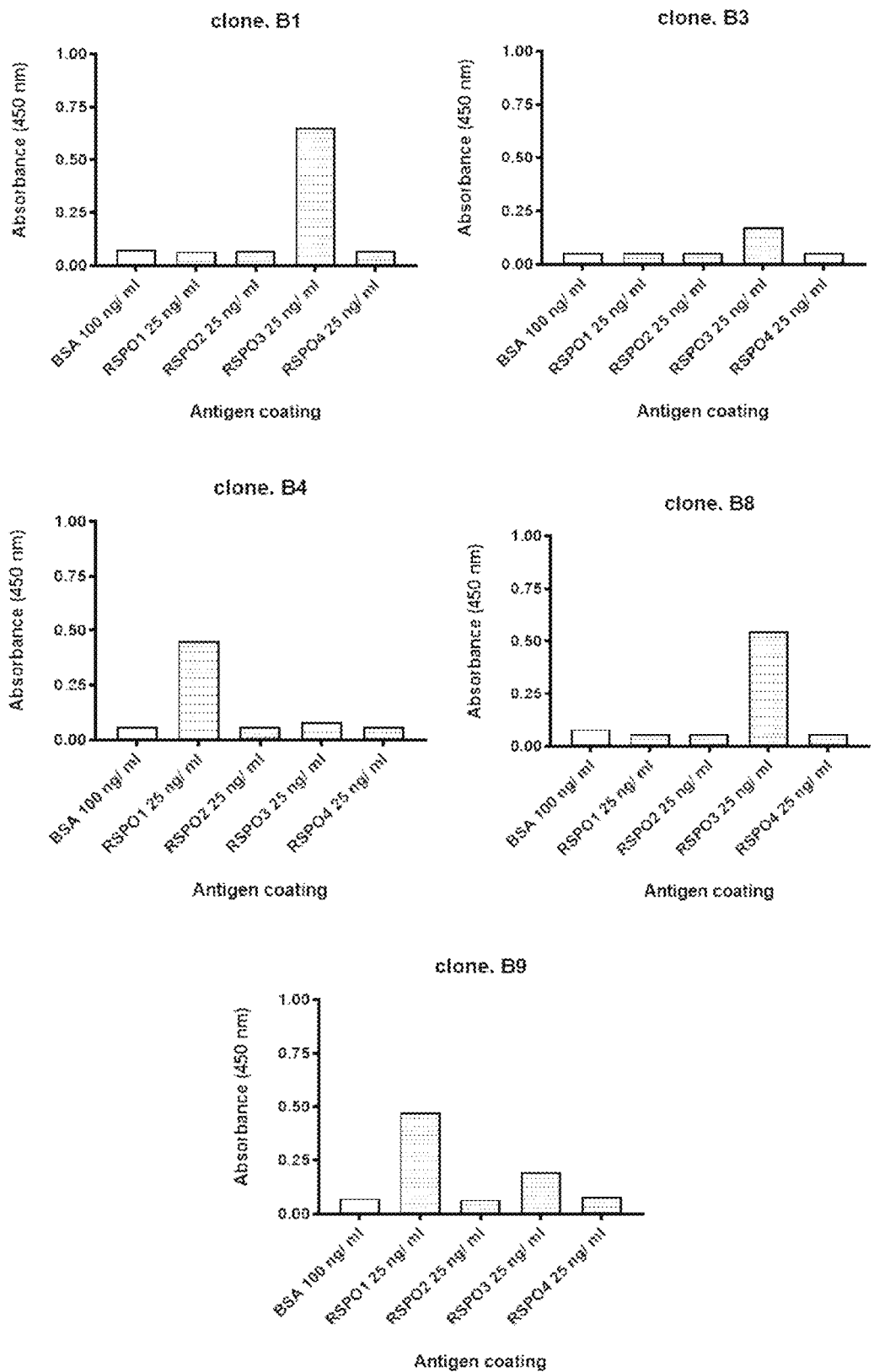

To assess the RSPO-binding capability of antibodies, purified monoclonal antibodies (mAbs) from several clonal hybridoma's culture supernatants originated from the initial batch-A clones (A1, A2, A4, A5, A6, A9) and batch-B clones (B1, B3, B4, B8, and B9) were reacted with RSPO1, 2, 3, and 4 on immunoblots. All mAbs from the initial batch-A clones showed strong reactivity with RSPO3. See FIG. 2, (A). Only B4 and B9 mAbs showed reactivity with RSPO3. See FIG. 2, (B). All of the RSPO3-reacted mAbs were then assessed for their selectivity in binding among the 4 different RSPOs, RSPO1-4. Results showed that mAbs derived from clones A1, A2, A4, A6, B1 and B8 only reacted with RSPO3 in ELISA assay. See FIG. 3.

To assess the RSPO3-binding affinities of the antibodies, kinetics assays were performed by the Octetsystems. The purified monoclonal antibodies (mAbs) from batch-A clones (A1, A4, A6, A9), along with the reference Ab-131R002, were examined for binding with RSPO-3. See Table 3. All those anti-RSPO3 antibodies from batch-A clones exhibited high on-target binding affinities ranging from $1.04 \times 10^{-8}$ to $7.8 \times 10^{-8}$ M.

TABLE 3

Binding affinities between RSPO3 proteins and Anti-RSPO3 Antibodies

| Sample ID | kon(1/Ms) | kdis(1/s) | KD (M) | KD Error | RMax |
|---|---|---|---|---|---|
| 131R002 | 1.05E+06 | 2.02E−03 | 1.93E−09 | 4.78E−11 | 0.1485 |
| A6 | 2.41E+05 | 2.50E−03 | 1.04E−08 | 3.57E−10 | 0.2151 |
| A4 | 3.27E+04 | 8.84E−04 | 2.70E−08 | 4.82E−09 | 0.3588 |
| A9 | 2.70E+04 | 1.13E−03 | 4.20E−08 | 7.12E−09 | 0.1496 |
| A1 | 2.83E+04 | 2.21E−03 | 7.80E−08 | 3.80E−09 | 0.2876 |
| Erbitux | 2.55E+01 | 2.49E−02 | 9.76E−04 | 4.17E−02 | 9.7173 |

Example 3

Inhibition of RSPO3-Wnt Signaling Pathway

Figure 4A:
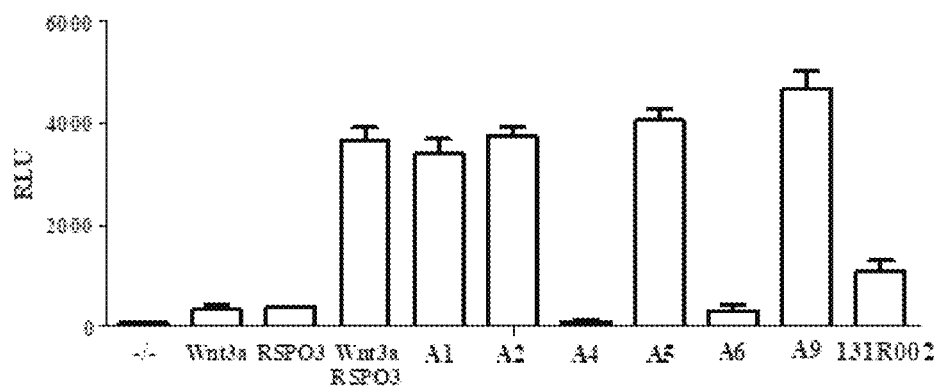
FIG. 4 is a set of graphs showing RSPO3 Abs targeting the canonical Wnt signaling and in vitro testing for inhibition of β-catenin activity. (A) A1, A2, A4, A5, A6, and A9 clones; (B) B1, B3, B4, B8, and B9 clones; and (C) Dose-response effect of elevated A4 and A6 clones on RSPO-Wnt signaling. MDA-MB436 TCF/LEF-Luc cells were incubated with a combination of Wnt3a (20 ng/mL) and RSPO3 (50 ng/mL) in the presence of 20 μg/mL anti-RSPO3 antibodies clone A1, A2, A4, A5, A6, A9 or 131R002. As controls, cells were incubated with a combination of Wnt3a and RSPO3, Wnt3a only, RSPO3 only, or with no addition. The cells were incubated for 16 hours and the luciferase activity assay was performed using One-Glo Luciferase Assay System.
Figure 4B:
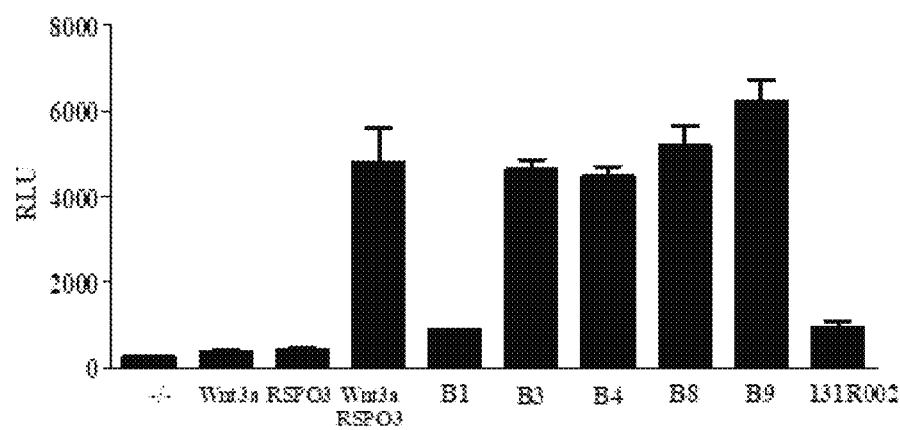
Figure 4C:
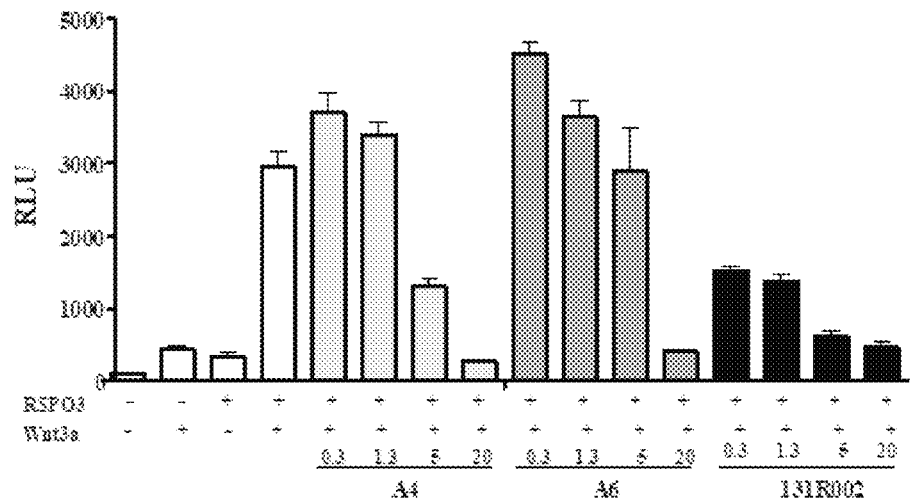

OncoMed Pharmaceuticals Inc. has developed several RSPO3-binding antibodies (rosmantuzumab (131R010) and 131R002). To serve as reference controls for our studies, antibodies Rosmantuzumab and 131R002 were constructed and expressed in accordance with the amino acid sequences released in publications (US22014/0017253A1). Subsequently, six in-house developed murine mAbs (A1, A2, A4, A6, B1, B8) and the 131R002 reference mAb were characterized in a number of bioassays. These α-RSPO3 murine mAbs exhibited substantial inhibitory activity towards RSPO-LGR signaling pathway. See FIGS. 4, (A) and (B). Only clones A4, A6 and B1 were found to exhibit significantly inhibitory effect in a dose-dependent manner in MDA-MB436 reporter cell lines harboring the RSPO3-Wnt downstream signaling pathway TCF/LEF-Luc reporter system. See FIG. 4. (C). Antibody isotyping was then performed to identify the class and subclass. Clones A4, A6 and B1 were found to be of isotype IgG1, IgG2a and IgG1, respectively, as shown in Table 4.

TABLE 4

Antibody isotyping

| Capture Antibody | A4 | A6 | B1 |
|---|---|---|---|
| IgG1 | ++++ | − | ++++ |
| IgG2a | − | ++++ | − |
| IgG2b | + | − | − |
| IgG3 | − | − | − |
| IgA | − | − | − |
| IgM | − | − | − |
| Kappa light chain | ++ | ++ | ++ |
| Lambda light chain | − | − | − |

Example 4

Humanization of α-RSPO3

The mRNA sequences of mAbs from hybridoma's were sequenced followed by cDNA synthesis and expression in CHO cells. After expression and purification of recombinant IgG's corresponding to A4, A6, and B1 hybridoma, these IgG's were confirmed for RSPO3 binding and neutralization. Clone B1 was selected for humanization. The murine mAb was humanized by variable domain resurfacing method with the aid of molecular modeling. See, e.g., Safdari et al. (2013). Biotechnol Genet Eng Rev (29): 175-186. The humanization technology also involves grafting of complementary determining region (CDRs) from murine to human IgG backbone and removal of T cell epitopes in the variable region sequences of antibodies to avoid the human anti-mouse antibody (HAMA) response for reducing potential immunogenicity in patients. The humanized α-RSPO3 mAb was then expressed in CHO cells and the purified antibody was analyzed for binding affinity and various in vitro and in vivo examination. See, e.g., Liu et al. (2008). Immunol Rev (222): 9-27. Results from the following sections confirmed the success of antibody engineering to yield a humanized α-RSPO3 antibody, hB1, derived from the murine clone B 1.

Figure 6A:
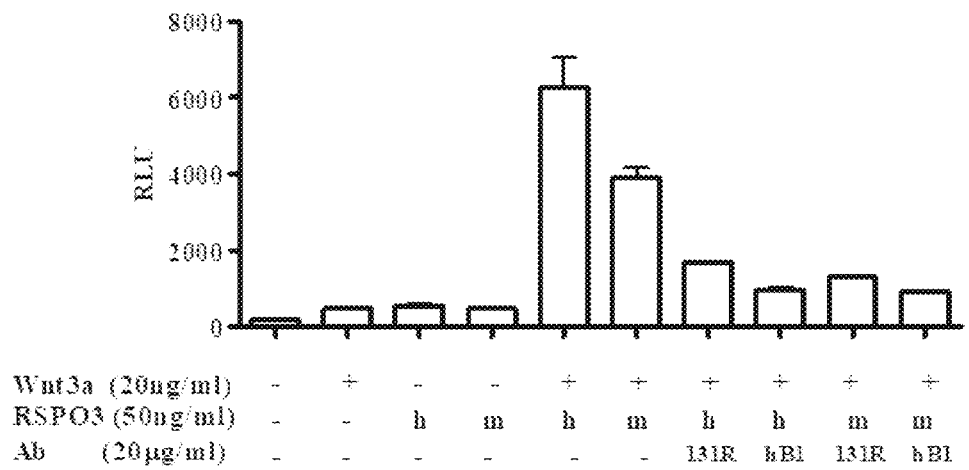
FIG. 6 is a set of graph showing that anti-RSPO3 Ab inhibits WNT reporter activity stimulated by combination of Wnt3a and RSPO3. (A) Dose-response inhibition of RSPO-Wnt signaling, stimulated by Wnt3a plus human RSPO3 (h) or murine RSPO3 (m), by hB1 or 131R010; and (B) MDA-MB436 TCF/LEF-Luc cells were incubated with a combination of Wnt3a (20 ng/mL) and hRSPO3 (50 ng/mL) in the presence of 20 ug/mL anti-RSPO3 antibodies clone hB1 or 131R010. The cells were incubated for 16 hours. The luciferase activity assay was performed using One-Glo Luciferase Assay System.
Figure 6B:
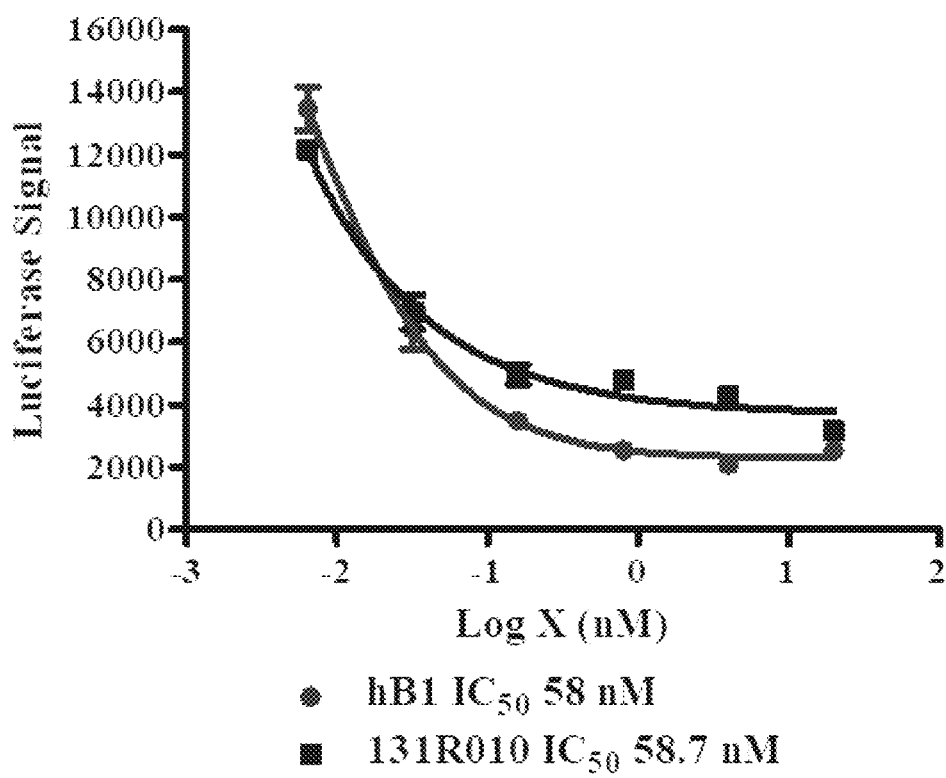

Example 4 hB1 and Rosmantuzumab Showed Equal Potency in RSPO-WNT Neutralization Assay and Antigen Binding Kinetics Assay The in vitro and in vivo anti-cancer activity of hB1, the lead candidate, were characterized and compared with rosmantuzumab that is undergoing Phase 1a/1b clinical trial. The hB1 mAb was generated based on human RSPO3 (hRSPO3) as the antigen. It was important to know whether hB1 can also recognize and neutralize murine RSPO3 (mRSPO3) because most preclinical in vivo studies will be conducted in mice. The amino acid sequence alignment between hRSPO3 and mRSPO3 is shown in FIG. 5. hB1 was able to inhibit the WNT reporter activity as stimulated by either hRSPO3 or mRSPO3. See FIG. 6, (A). The concentrations of hB1 and rosmantuzumab required for 50% of maximal inhibitory inhibition ($IC_{50}$) were 58.0 and 58.7 nM, respectively, as shown in the WNT reporter assay. See FIG. 6, (B).

Figure 7:
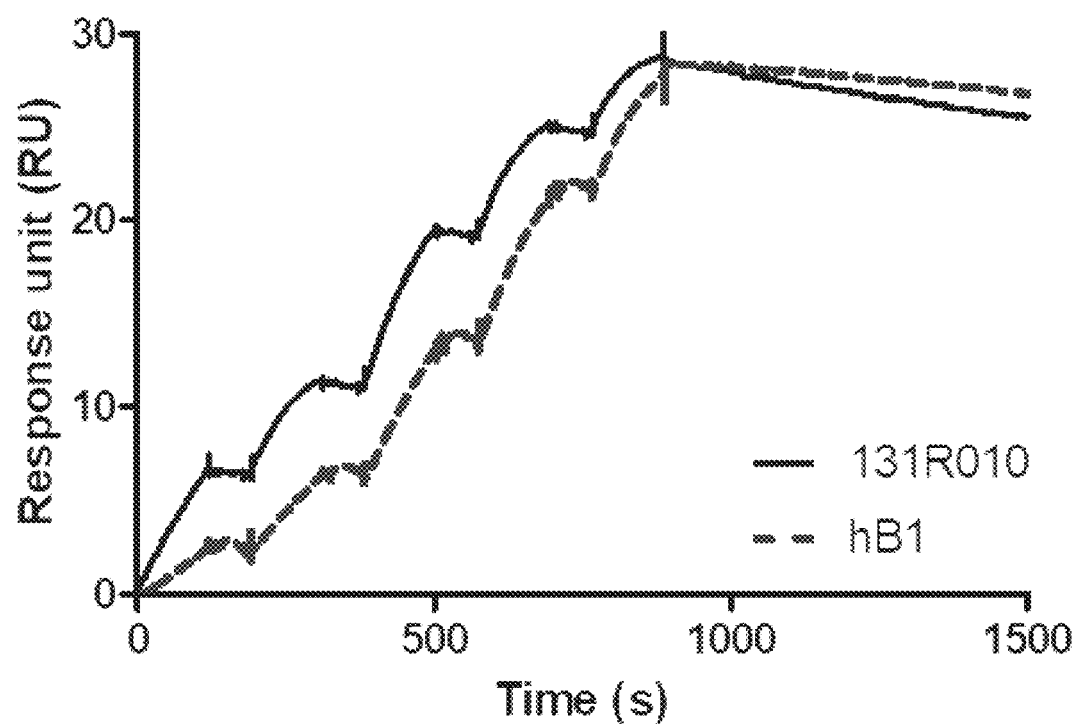
FIG. 7 is a graph showing use of Biacore to measure the binding kinetics of α-RSPO3 Abs-antigen interaction. The binding sensorgrams were generated using a Biacore T200 and then fitted to a simple 1:1 interaction model. A series of concentrations of hB1 (0.39-6.25 nM) were injected in a single-cycle with no regenerating of the surface between injections. The association was monitored for 2 min, and the final dissociation time was 15 min hRSPO3 was immobilized on a CM5 chip at 27.5 RU.

To measure the binding characteristics of hB1 to hRSPO3, kinetics assays were performed using Biacore T200. hRSPO3 protein was immobilized on CM5 sensor chips with coating densities of approximate 27.5 response units (RU). As shown in FIG. 7, the binding affinity of hB1 with hRSPO3 is similar to the binding affinity of rosmantuzumab with hRSPO3. The equilibrium dissociation constants, KD, were both at picomolar (pM) levels. See Table 5.

TABLE 5

Characterization of binding kinetics of antibody-antigen interactions using Biacore biosensors.

| ID | $k_{on}$ (1/Ms, *$10^6$) | $k_{off}$ (1/s, *$10^{-5}$) | KD (pM) |
|---|---|---|---|
| 131R010 | 9.4 ± 1.8 | 18.1 ± 0.1 | 20.0 ± 0.4 |
| hB1 | 1.7 ± 0.8 | 3.4 ± 0.1 | 26.8 ± 1.3 |

Example 5

Mapping of Binding Epitopes

Figure 8A:
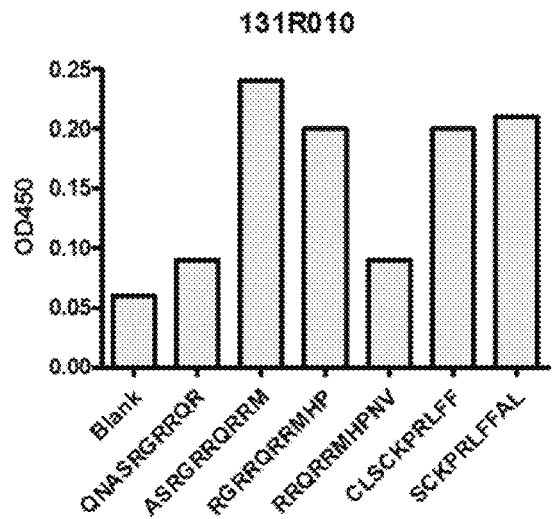
FIG. 8 is a set of graphs showing mapping of the α-RSPO3 Ab epitopes on RSPO3 protein by Pep-set. These histograms represent the ability of each 10-mer oligopeptide to bind the RSPO3 Abs 131R010(A), 131R002 (B), and hybridoma A6 (C) as indicated in the figure. QNASRGRRQR (SEQ ID NO: 74); ASRGRRQRRM (SEQ ID NO: 75); RGRRQRRMHP (SEQ ID NO: 84); RRQRRMHPNV (SEQ ID NO: 76); CLSCKPRLFF (SEQ ID NO: 77); SCKPRLFFAL (SEQ ID NO: 78); ERGKKGRERK (SEQ ID NO: 79); GKKGRERKRK (SEQ ID NO: 80); KGRER-KRKKP (SEQ ID NO: 81); RERKRKKPNK (SEQ ID NO: 82); RENKQQQKKR (SEQ ID NO: 83).
Figure 8B:
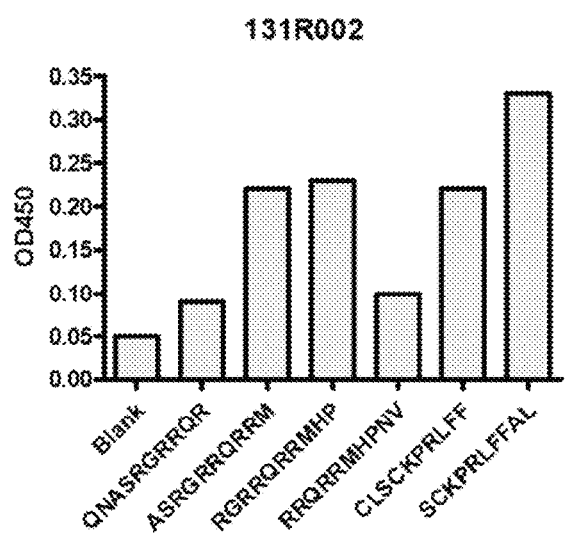
Figure 8C:
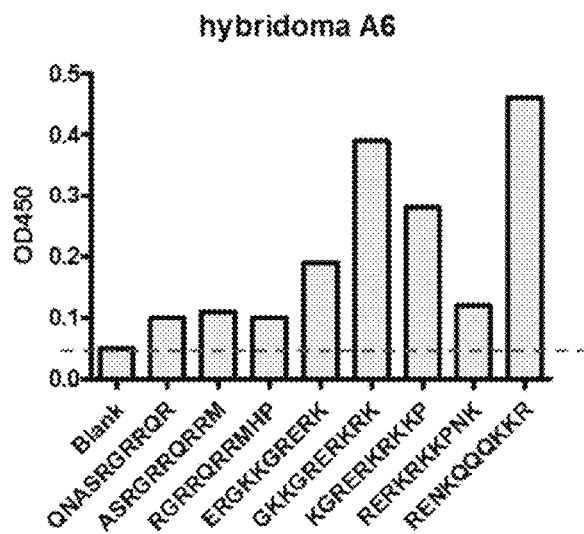

To identify the binding epitopes of α-RSPO3 Abs, an overlapping peptide library (10-mer for each peptide, offset: 2 amino acid residues, total number of peptides to cover the mature hRSPO3:122) derived from hRSPO3 amino acid sequences was prepared by Mimotope, Inc. The binding of α-RSPO3 mAbs to the overlapping peptides derived from hRSPO3 was measured. The amino acid sequences identified as probable binding epitopes are shown in Table 6. The reference antibodies including 131R002 and rosmantuzuma reacted with amino acid (a.a.) 7-11 and a.a. 35-42 from RSPO3 fragments, and hybridoma A6 α-RSPO3 mAb reacted with a.a. 5-11, 35-42 and 195-198 of RSPO3 sequences. However, neither the A4 nor the hB1 mAbs showed detectable binding signals. The results suggest that hB1 and rosmantuzuma recognize different binding epitopes on hRSPO3. According to the epitope mapping results using linear peptides (FIG. 8 and Table 6), it was concluded that hB1 likely binds to a conformationlly-determined epitope on huRSPO3. This observation was important to demonstrate the different binding modes between hB1 and rosmantuzuma.

TABLE 6

Epitope mapping for α-RSPO3 mAbs by peptide scanning

| Abs | Signal | Sequences |
|---|---|---|
| 131R002 | + | R7-R11; S35-F42 |
| 131R010 | + | R7-R11; S35-F42 |
| hybridoma A6 | + | R5-R11; S35-F42; R195-K198 |
| hybridoma A4 | − | |
| hB1 | − | |

Figure 9A:
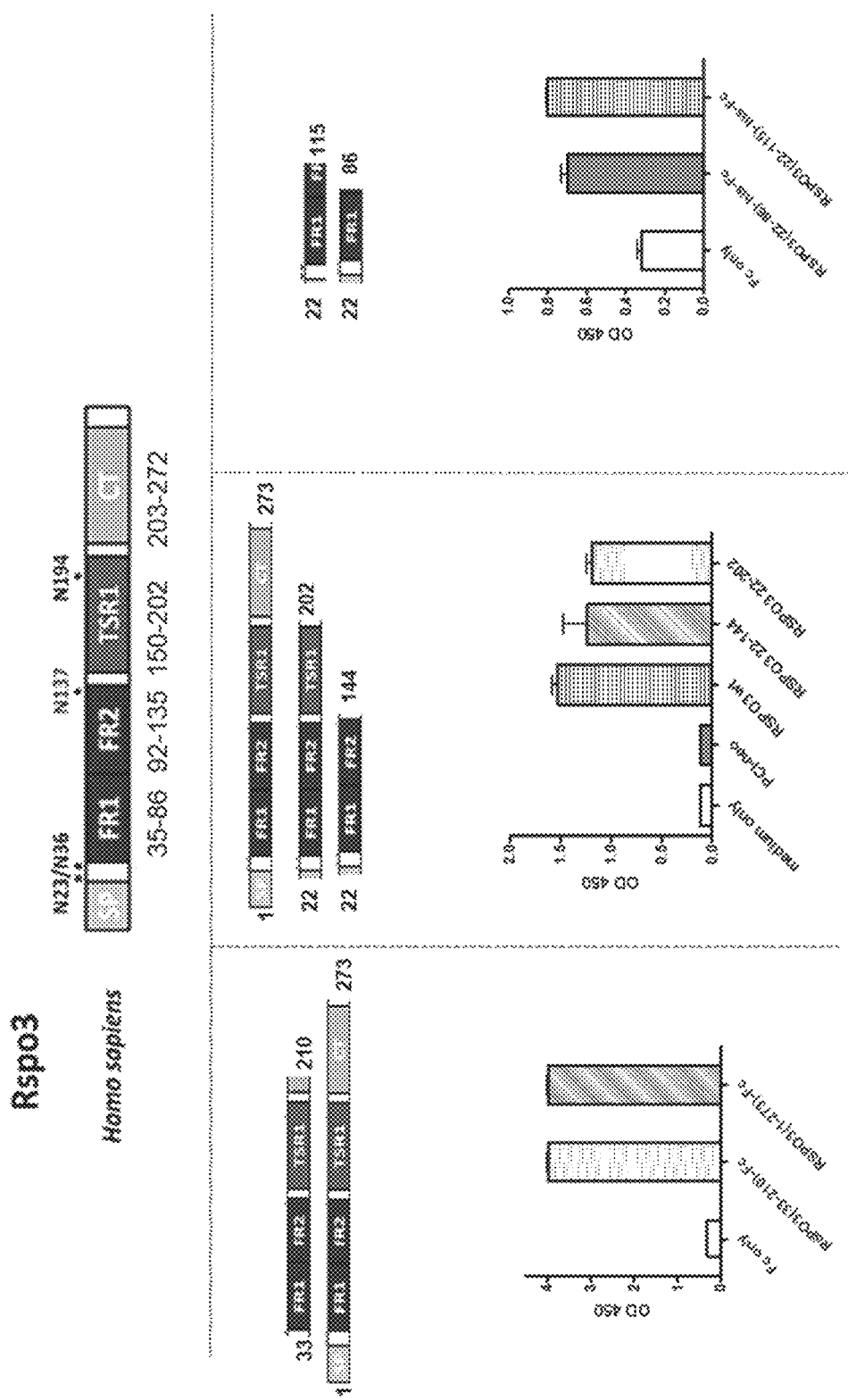
FIG. 9 is a set of schematics and graphs showing epitope studies of several α-RSPO3 antibodies. (A) Various truncated RSPO3 fragments were coated on ELISA plates, followed by the addition of biotinylated hB1, an α-RSPO3 antibody, to each well. Streptavidin-HRP was then added for detection of the bound biotinylated antibody. (B) The biotinylated cyclic peptides, at 1 μg/ml, and biotinylated recombinant human RSPO3, at 100 ng/ml, were applied to NeutrAvidin pre-coated plates. To examine the binding between different cyclic peptides and hB1, hB1 at 2 μg/ml was then added to each well of the plates. To detect bound anti-RSPO3 antibodies, Goat anti-human IgG-Fc-HPR (Chemicon) was then applied to the plates.
Figure 9B:
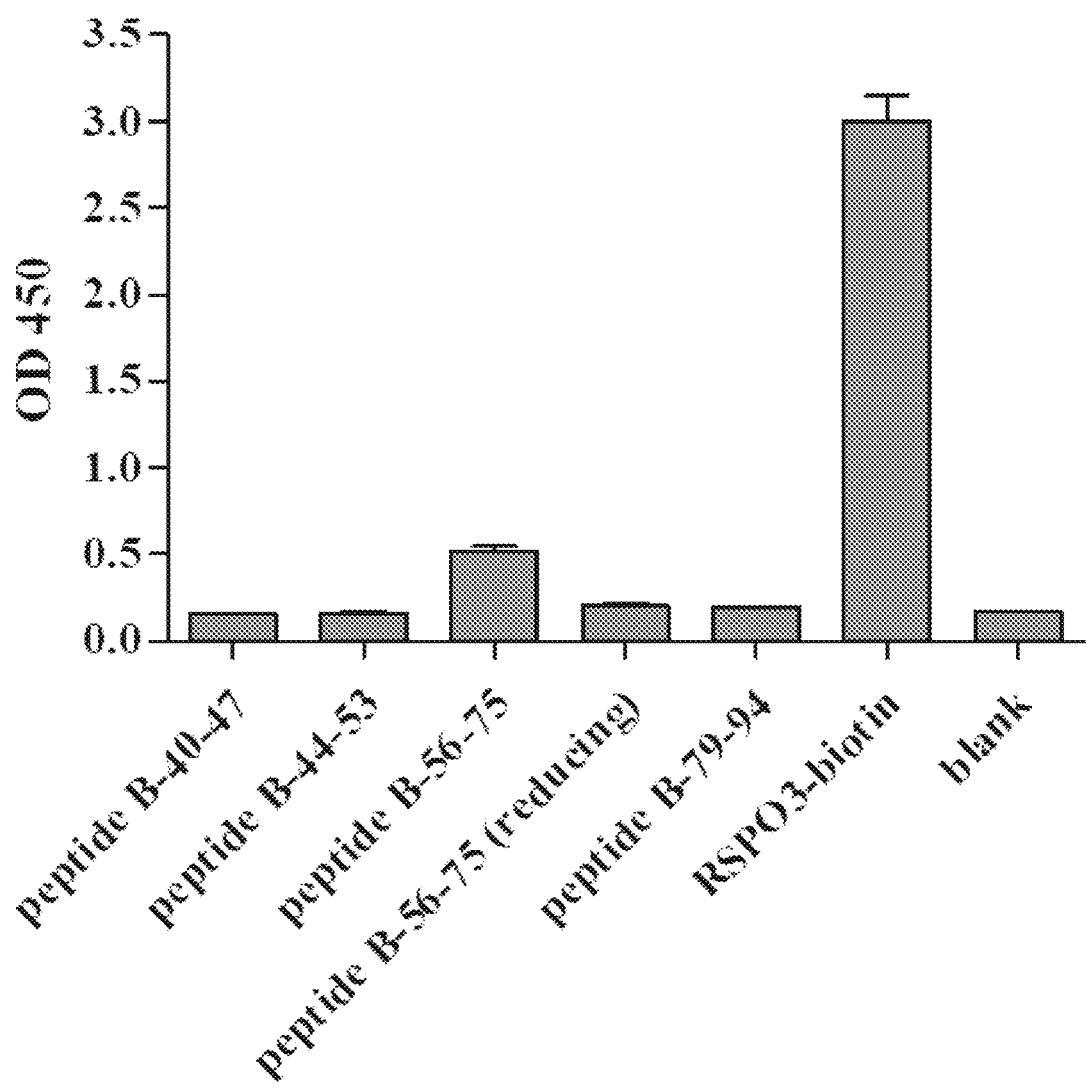

Further conformation epitope studies of α-RSPO3 Abs were performed using recombinant RSPO3 truncated proteins and cyclic peptides scanning to narrow down their target sequences. The results demonstrated that hB1 recognized c-terminal truncated regions in the RSPO3 protein. The binding epitope of hB1 in RSPO3 was narrowed down to a.a. 33-86. See FIG. 9, (A). RSPO3 contains a furin-like cysteine-rich region. Until now, the 3D structure of RSPO3 has not been reported. Additionally, four cyclic peptides (a.a. 40-47, 44-53, 56-75 and 79-94) were designed to measure the binding of α-RSPO3 mAbs to the cyclic peptides derived from hRSPO3. The results demonstrated that hB1 recognizes selected epitopes containing domains in the RSPO3 FR1 region (including residues 56-75). See FIG. 9, (B). hB1 may target a novel epitope in the RSPO3 furin region (including residues 56-75) to neutralize the RSPO-WNT pathway.

Example 6 hB1 Competed with LGR5 and Bound to RSPO3

To exam whether different α-RSPO3 antibodies competed with LGR5 or RNF43 to the binding of RSPO3, the Ab/receptor/ligand binding competition ELISA assay was performed. 131R010 and 5D6 were from Oncomed and Genetech as α-RSPO3 reference antibodies. The ELISA-based analysis of the interaction between different α-RSPO3 antibodies and LGR5 surface receptor to compete with RSPO3 at the receptor binding site is presented.

Figure 10A:
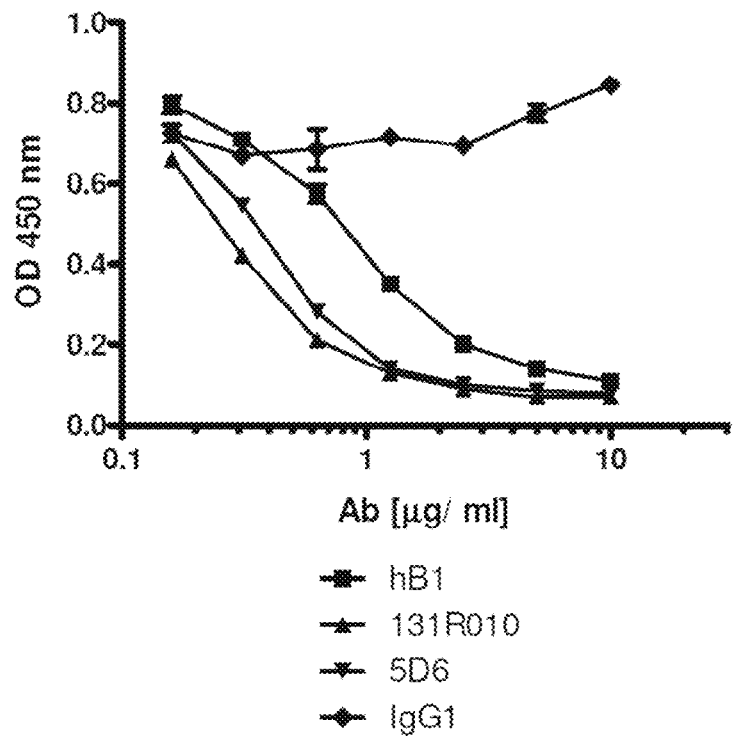
FIG. 10 is a set of graphs showing competitive binding of RSPO3 to LGR5 or RNF43 by different α-RSPO3 antibodies. To exam whether different α-RSPO3 antibodies might compete with the binding of RSPO3 to LGR5 or RNF43, recombinant hRSPO3 was coated on a plate. (A) Recombinant LGR5 (22-560)-Fc was conjugated with biotin to facilitate detection. Biotinylated LGR5 was then respectively mixed with various concentrations of either α-RSPO3 antibodies or isotype control Ab and applied to RSPO3-coated wells. Streptavidin-HRP was then added to detect bound biotinylated LGR5; and (B) Mixtures of recombinant His-tagged RNF43 and different α-RSPO3 antibodies, respectively, were applied to each RSPO3-coated wells. Mouse anti-His tag antibody-HRP was then added for detection of bound RNF43. After removing extra detection antibodies by washing the plates with 1×PBST, a TMB substrate solution was added to each well for 10 minutes. The colorimetric reaction was then stopped by 2N HCL and the optical density at 450 nm of each well was determined immediately.
Figure 10B:
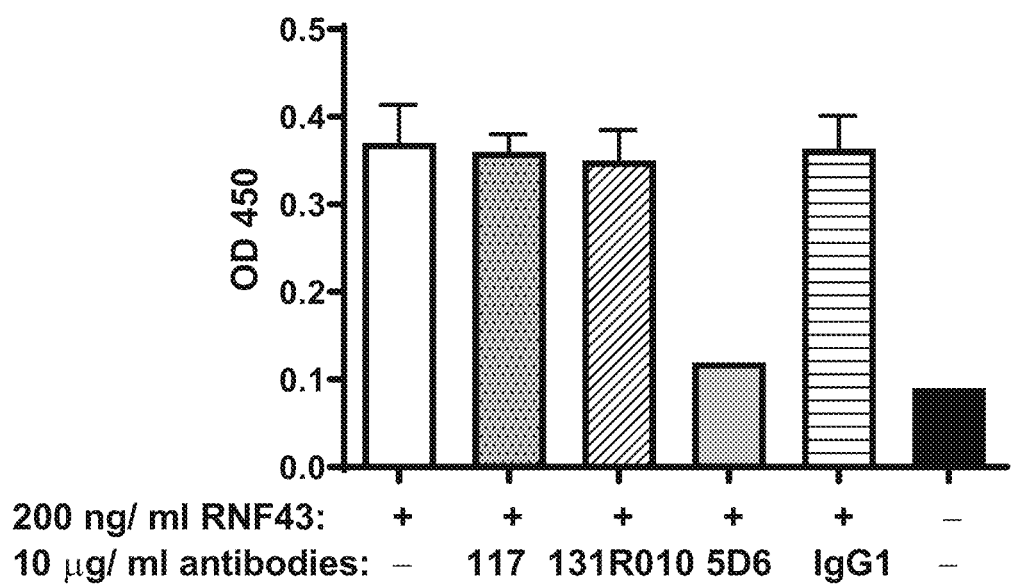

The results demonstrated that these α-RSPO3 antibodies competed with LGR5 and bound to RSPO3 as compared to the control Ab group. See FIG. 10, (A).

Additionally, the competition receptor/ligand competition assay for determining the binding capacity of co-receptor RNF43 at their receptor binding site was designed. Our results demonstrated that hB1 and 131R010 did not interfere with the binding between RNF43 and RSPO3. 5D6 competed with LGR5 and RNF43 and bound to huRSPO3. See FIG. 10, (B). Our results demonstrated that neutralization of RSPO3 by hB1 markedly reduced WNT/β-catenin signaling pathway activation contributions from LGR5-dependent pathways.

Figure 11:
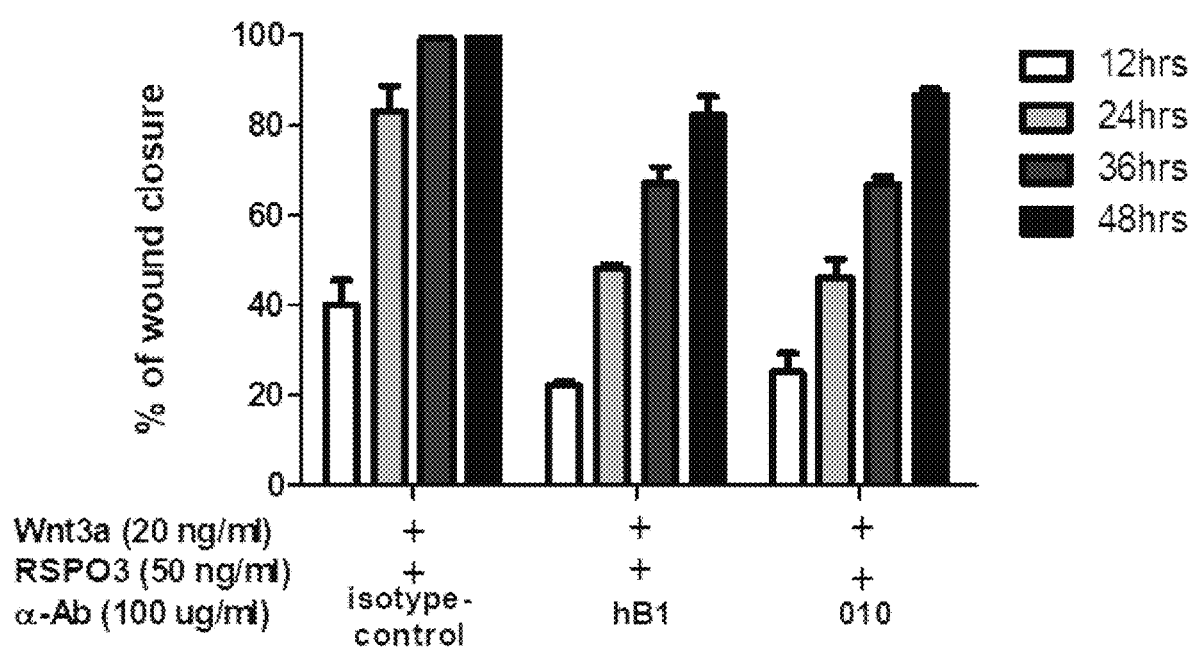
FIG. 11 is a graph showing the effects of different α-RSPO3 antibodies on wound healing in the DLD-1 cell model. The percentages of wound closure were calculated and shown in the bar graph.

Example 7

α-RSPO3 Abs Inhibited Cell Migration Capacity of Human Colorectal Adenocarcinoma DLD-1 Cells Since RSPO3-Wnt signal cascade regulates not only cell invasion but also cell migration, a wound healing assay was performed to examine how α-RSPO3 mAbs may affect migration capacity. Wnt3a and RSPO3 treatment enhanced migratory activity of DLD cells (harboring deletions in the adenomatous polyposis coli (APC) gene). The effects of an isotype control Ab and hB1 on the migratory activity of DLD-1 in the presence of Wnt3a and RSPO3 treatment were compared. It was found that found that both hB1 and 131R010 α-RSPO3 mAbs were able to inhibit wound healing activity of DLD-1 cells in the presence of Wnt3a and RSPO3. See FIG. 11.

Example 8 hB1 Inhibited CR3150 PDX Tumor Growth

Figure 12:
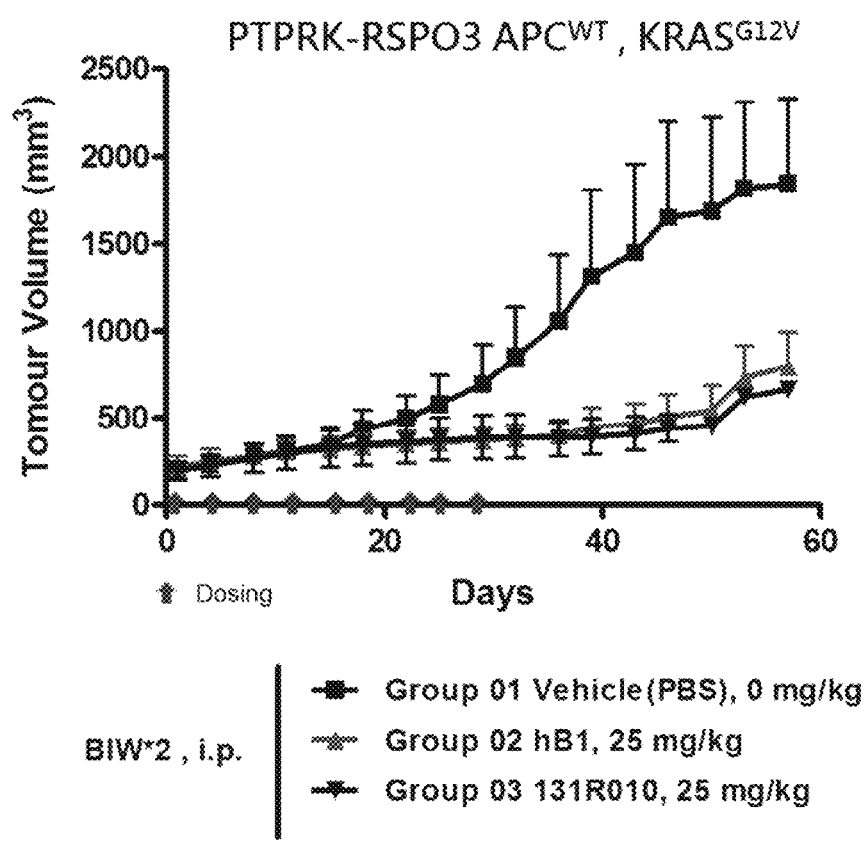
FIG. 12 is a graph showing inhibition of colorectal cancer PDX model CR3150 tumor growth in vivo using specific anti-RSPO3 monoclonal antibodies. Mice were treated with hB1, 131R010, or control (vehicle (PBS)) twice weekly for 4.5 weeks. On Day 5 of treatment, 3 mice from each of the vehicle and hB1 groups were sacrificed for tumor collection at 24 hours after the second dose. Since then from Day 5 to 58, there were remaining 5, 3, and 3 mice in the control, hB1 or 131R010 groups, respectively. Data are expressed as mean±SEM. One mouse in the vehicle group and one in the untreated group were euthanized on Day 39 and Day 46, respectively, due to tumor volume reaching humane endpoint, and the last value of the tumor volume was carried forward until the end of the study.

The CR3150 colon tumor was derived from a 35-year-old Asian female patient. CR3150 tumor is a moderately differentiated tubular adenocarcinoma harboring a PTPRK-RSPO3 fusion gene. Tumor-bearing mice were initially allocated into four experimental groups, i.e., vehicle (PBS), hB1, 131R010 and untreated group. The test articles or vehicle were injected i.p. to mice twice weekly from day 1 through day 29. As shown in FIG. 12, mean tumor volume of the control group reached 1867.6±475.7 mm³ at study termination on day 58 post-treatment. The group treated with hB1 at 25 mg/kg induced apparent tumor growth inhibition (TGI=60.8%, p=0.179) with terminal average tumor volume of 871.2±227.7 mm³. See FIG. 12. The group treated with 131R010 at 25 mg/kg also produced antitumor activity (TGI=71.0%, p=0.067) with terminal average tumor volume of 680.2±38.2 mm³. See FIG. 12. On Day 46, when differences between treatment and control were compared using relative tumor volume, statistical significant antitumor activity was recorded as TGI=68.4%, p=0.041, for treatment of hB1, and TGI=69.8%, p=0.039, for treatment of 131R010. Thus, hB1 and 131R010 were believed to have therapeutic benefit in this study. Also, there was no severe body weight loss in this study. In summary, hB1 and 131R010 dosed as single agent demonstrated significant antitumor activity against the CR3150 patient-derived colorectal cancer model.

Example 9

α-RSPO3 Abs Reduced Molecular Responses in the CR3150 PDX Models

Figure 13:
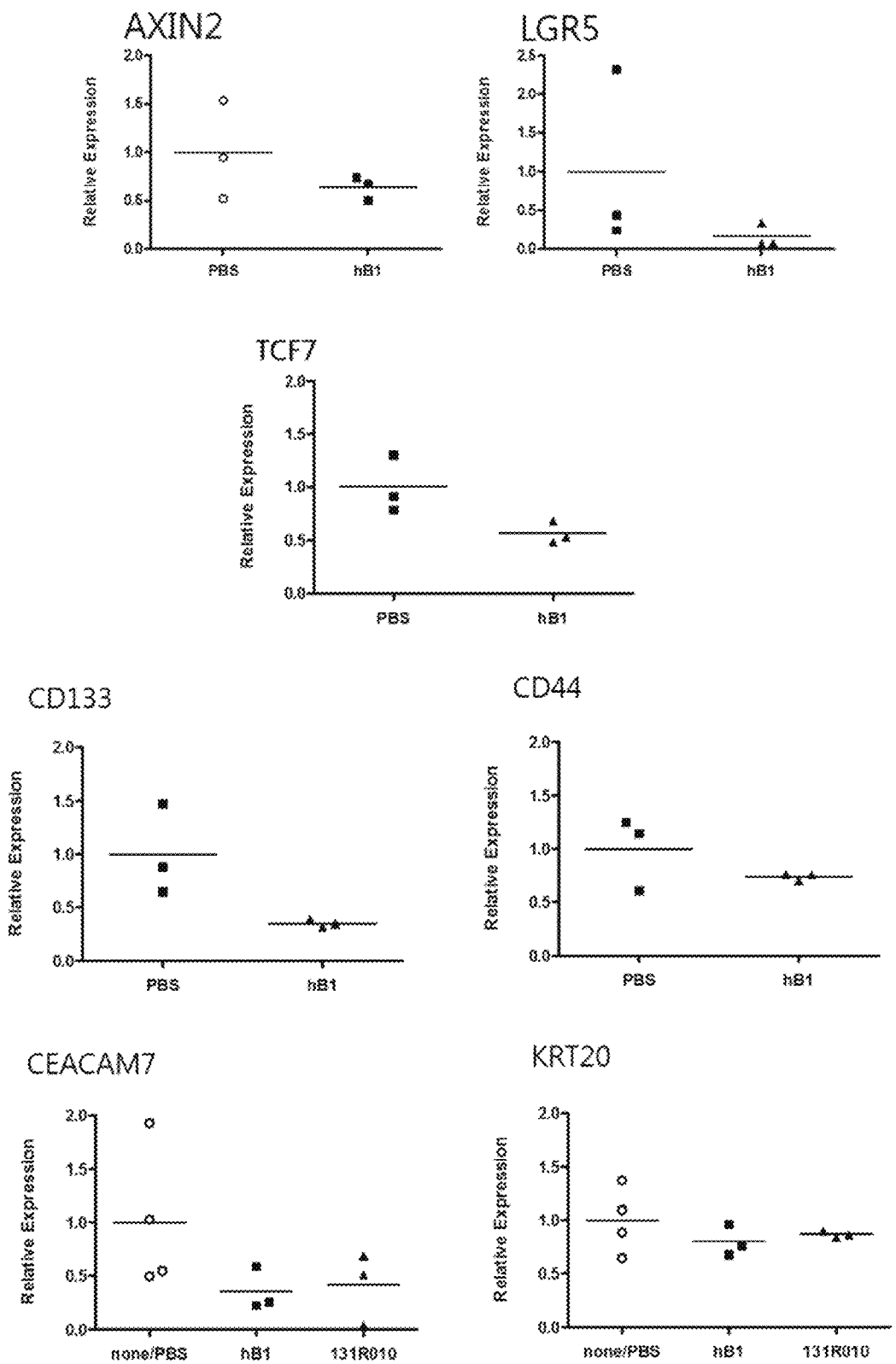
FIG. 13 is a set of graphs showing evaluation of molecular responses of hB1 in CR3150 PDX models. The expression of intestinal stem cell markers (Axin2 and LGR5), downstream markers (TCF7), cancer stem cell markers (CD133 and CD44) and differentiation markers (CEACAM7 and KRT20) were performed using Q-PCR within 2 days after 2 doses or 29 days after the last dose.

To evaluate molecular responses of hB1 in CR3150 PDX models, the expression levels of the intestinal stem cell markers (Axin2 and LGR5), Wnt downstream markers (TCF7), cancer stem cell markers (CD133 and CD44) and differentiation markers (CEACAM7 and KRT20) were measures. Results showed that the expression of intestinal stem cell markers (Axin2 and LGR5) and a Wnt downstream marker (TCF7) in the hB1 treatment group were significantly lower than the control group at the early stage. See FIG. 13. The expression of cancer stem cell markers (CD133 and CD44) and differentiation markers (CEACAM7 and KRT20), analyzed within 29 days after the last dose of the in-house RSPO3 Ab group, was significantly reduced compared to the control group. See FIG. 13.

Example 10

α-RSPO3 Abs Inhibited NCI-H2030 RSPO$^{high}$ CDX Model Tumor Growth

Figure 14:
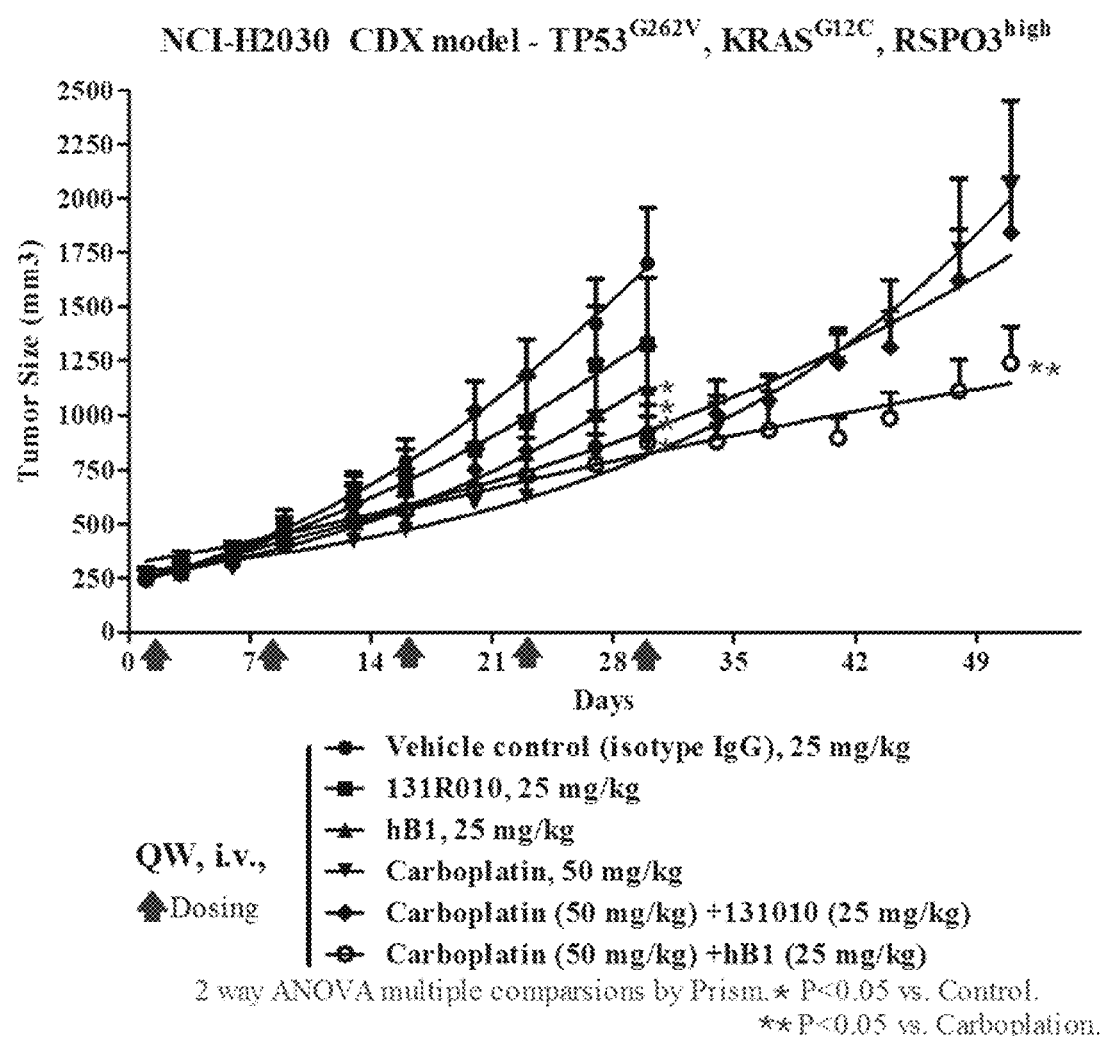
FIG. 14 is a graph showing the efficacy of hB1 in a RSPO$^{high}$ NCI-H2030 Lung Cancer CDX model. Mice were treated with hB1 or 131R010 at 25 mg/kg, or control (vehicle) once a week for 4 weeks. On Day 28 of treatment, 7 mice from each of the vehicle, 131R010 and hB1 groups were sacrificed for tumor collection at 24 hours after the fifth dose. Data are expressed as mean±SEM. On Day 51 of treatment, 7 mice from each of the Carboplatin, hB1, 131R010 and carboplatin in combination groups were sacrificed for tumor collection. Data are expressed as mean±SEM.

The NCI-H2030 lung cancer cell was derived from the lymph node of a lung cancer patient. NCI-H2030 cells were shown to have RSPO3 overexpression. Tumor-bearing mice were initially allocated into six experimental groups to receive: 1) vehicle, 2) hB1, 3) 131R010, 4) carboplatin+vehicle, 5) carboplatin+hB1, and 6) carboplatin+131R010. See FIG. 14. The test articles or vehicle were intravenously administered into the mice once a week from day 1 through day 29. On Day 29 post treatment, mean tumor volume of the control group reached 1702±298.1 mm³. The treatment of hB1 at 25 mg/kg induced apparent tumor growth inhibition with terminal average tumor volume of 1124±471.8 mm³. The treatment of 131R010 at the same dosage also produced antitumor activity with terminal average tumor volume of 1327.4±194.3 mm³. hB1 demonstrated therapeutic benefit in this study. Also, there was no severe body weight loss in this study. In summary, hB1 dosed as single agent or in combination with carboplatin demonstrated significant antitumor activity against the H2030 lung cancer CDX model. Furthermore, hB1 showed better anti-cancer efficacy than rosmantuzumab in the NCI-H2030 cancer xenograft model.

Example 11

α-RSPO3 Abs Inhibited Human SNU-1411 Colon Xenograft Tumor Carrying PTPRK(e13)-RSPO3(e2) Fusion Transcript The activity of anti-RSPO3 antibody hB1 was compared with reference anti-RSPO3 antibody OMP-131R10, alone and in combination with paclitaxel, in a human SNU-1411 colon xenograft tumor carrying PTPRK(e13)-RSPO3(e2) fusion transcript. The results of average tumor size in different groups during the course of study after treatment initiation are shown in FIG. 15. The mean tumor size of the control mAb group reached 1071 mm$^3$ on day 18. When used alone, 131R10 and hB1 had no antitumor activity against SNU-1411 tumor growth compared to the control treated group (p>0.05 vs. control mAb treated group by one-way ANOVA followed by Tukey's post-test comparison in both cases). See FIG. 15, top. The average tumor volumes were 1265 mm$^3$ for 131R10 and 1177 mm$^3$ for HB1 on day 18. Paclitaxel alone produced a 69% tumor volume reduction relative to the control mAb treated group on day 18 (p<0.05 vs. control mAb by one-way ANOVA followed by Tukey's post-test comparison). See FIG. 15, top. The combination of 131R10 plus paclitaxel and the combination of hB1 plus paclitaxel decreased tumor volume by 78% and 86%, respectively, as compared to the control mAb treated group on day 18 (p<0.05 vs. control mAb group by one-way ANOVA followed by Tukey's post-test comparison in both cases). See FIG. 15, top. There was no statistical significance between the two combination groups vs. paclitaxel alone (p>0.05 vs. paclitaxel group by one-way ANOVA followed by Tukey's pairwise comparison in both cases). See FIG. 15, top. Table 7 summarizes the anti-tumor efficacy of hB1, 131R10, paclitaxel and their combinations on day 18. In general, antibody treatments were well tolerated as single agents and in combination with paclitaxel.

Control mAb and anti-RSPO3 single agent groups were terminated 24 hours after the last dose on day 18. Treatment continued for animals in paclitaxel and combination groups to determine treatment response duration. The anti-tumor efficacy of paclitaxel was lost 3 weeks post treatment, reaching the average tumor volume of 950 mm$^3$ on day 32 (31 days post treatment). See FIG. 15. On the other hand, tumor growth inhibition was sustained by both combination groups, resulting in tumor volume reduction by 82% by 131R10 plus paclitaxel and 75% by hB1 plus paclitaxel vs. paclitaxel alone on day 32 (p<0.05 vs. paclitaxel by one-way ANOVA followed by Tukey's pairwise comparison. See FIG. 15, bottom. Table 8 summarizes the anti-tumor activity of paclitaxel and the combination groups on day 32 (31 days post treatment). Anti-tumor efficacy of the combinations was reduced from day 36 on. The average tumor volume at the conclusion of the study on day 46 was 874±247 mm$^3$ for hB1 plus paclitaxel and 399±138 mm$^3$ for 131R10 plus paclitaxel.

TABLE 7

Anti-tumor efficacy of 131R10 and hB1 as single agents and in combination with paclitaxel in human SNU-1411 colon xenograft tumor carrying PTPRK(e13)-RSPO3(e2) fusion transcript on day 18.

| Treatment | N | Tumor volume on day 18 | Tumor volume reduction, % of Control mAb |
|---|---|---|---|
| Control mAb | 7 | 1071 ± 152 | — |
| 131R10 | 7 | 1264 ± 153 | −18 ± 14 |
| hB1 | 7 | 1177 ± 228 | −10 ± 21 |
| Paclitaxel | 7 | 329 ± 59 | 69 ± 6* |
| 131R10 + Paclitaxel | 7 | 242 ± 101 | 78 ± 10* |
| hB1 + Paclitaxel | 7 | 156 ± 147 | 86 ± 4* |

*p < 0.05 vs. control mAb by one-way ANOVA followed by Tukey's post-test comparison

TABLE 8

Anti-tumor efficacy of 131R10, hB1 in combination with paclitaxel in human SNU-1411 colon xenograft tumor carrying PTPRK(e13)-RSPO3(e2) fusion transcript on day 32.

| Treatment | N | Tumor volume on day 32 | Tumor volume reduction, % of paclitaxel |
|---|---|---|---|
| Paclitaxel | 7 | 949 ± 105 | — |
| 131R10 + Paclitaxel | 7 | 176 ± 76 | 82 ± 8* |
| hB1 + Paclitaxel | 7 | 245 ± 88 | 75 ± 9* |

*p < 0.05 vs. paclitaxel by one-way ANOVA followed by Tukey's post-test comparison.

In summary, the present study demonstrated that treatment with hB1 or 131R10 alone for 2 weeks has no anti-tumor effect against human SNU1411 colon xenograft tumor carrying PTPRK(e13)-RSPO3(e2) fusion transcript but was efficacious in combination with paclitaxel with similar anti-tumor activity compared to paclitaxel treated group. Paclitaxel-mediated growth inhibition is lost 3 weeks post treatment, whereas the combination of either hB1 or 131R10 with paclitaxel remains efficacious 4 weeks post treatment. Tumor growth resumed 35 days post treatment for both combinations, with 131R10 plus paclitaxel at a slower rate than hB1 plus paclitaxel.

Example 12

Immunohistochemical Expression of RSPO3 in Breast Cancer, Colon Cancer, Pancreatic Cancer, and Lung Cancer Tissue Microarrays by α-RSPO3 Antibody hB1

Figure 16:
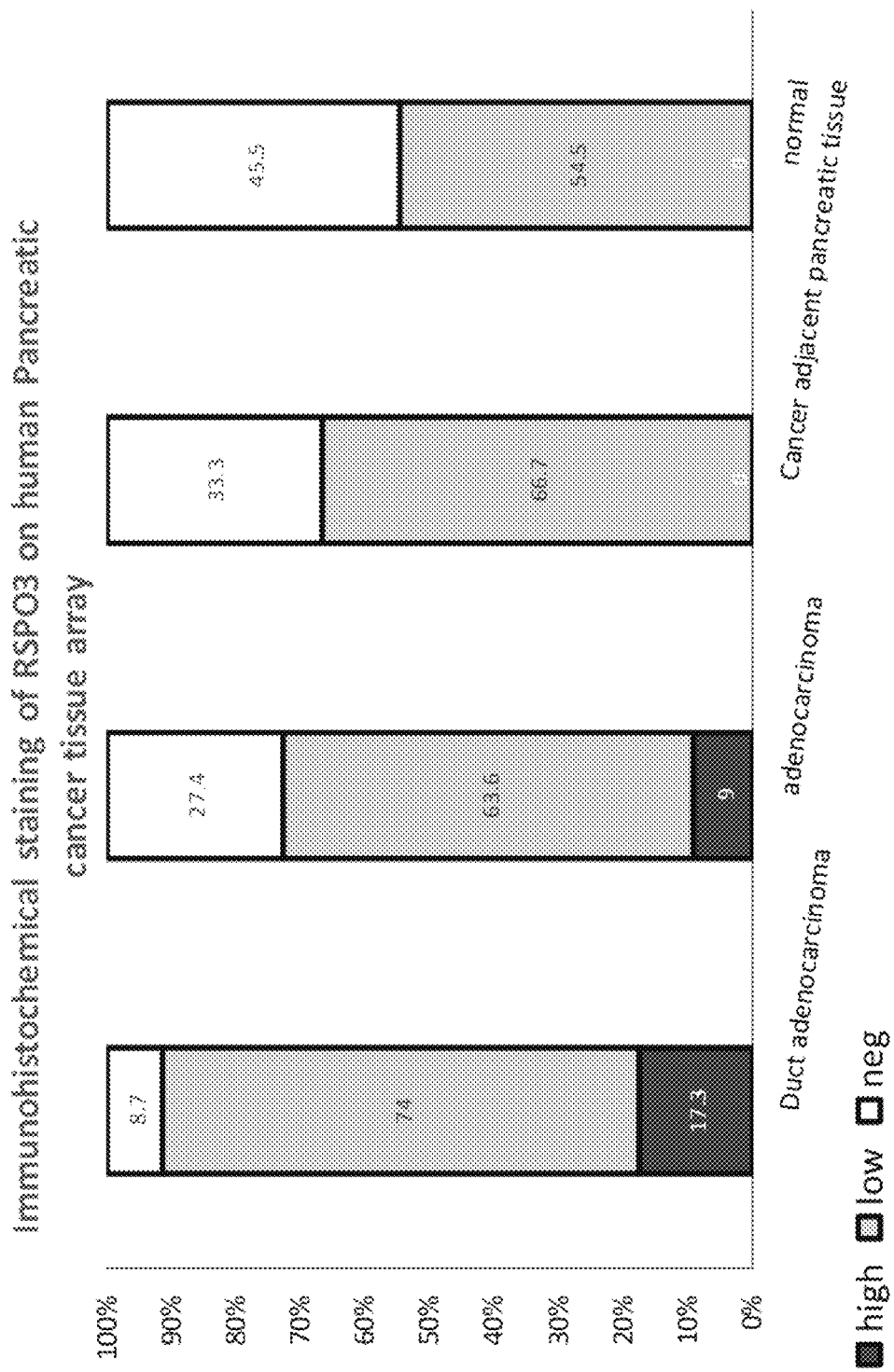
FIG. 16 is a graph showing expression of RSPO3 in pancreatic cancer tissues. A pancreatic cancer tissue microarray consisting of 80 patient samples was stained with the anti-RSPO3 mAb hB1. Images of whole sections were scanned by 3DHISTECH's digital slide scanner. The graph shows the percentages of cases expressing RSPO3 in the cancer tissue array and normal tissue array.

To assess differential expression of RSPO3 in normal and disease state cancer tissues, its association with pathologic features in patients with breast, colon, pancreatic, lung cancers was evaluated by tissue microarray (TMA)-based immunohistochemistry (IHC). The expression of RSPO3 in a 80 pancreatic adenocarcinoma and normal cases tissue array was evaluated by RSPO3 antibody hB1. The results showed that 91% (21/23) of tumors showed low to strong RSPO3 positive staining. In contrast, only 8.7% (2/23) showed negative staining in pancreatic duct adenocarcinoma cases. The results demonstrated that higher RSPO3 expression was more frequently observed in later TNM staging pancreatic duct adenocarcinoma compared to normal or cancer adjacent pancreatic tissues. See FIG. 16.

Figure 17:
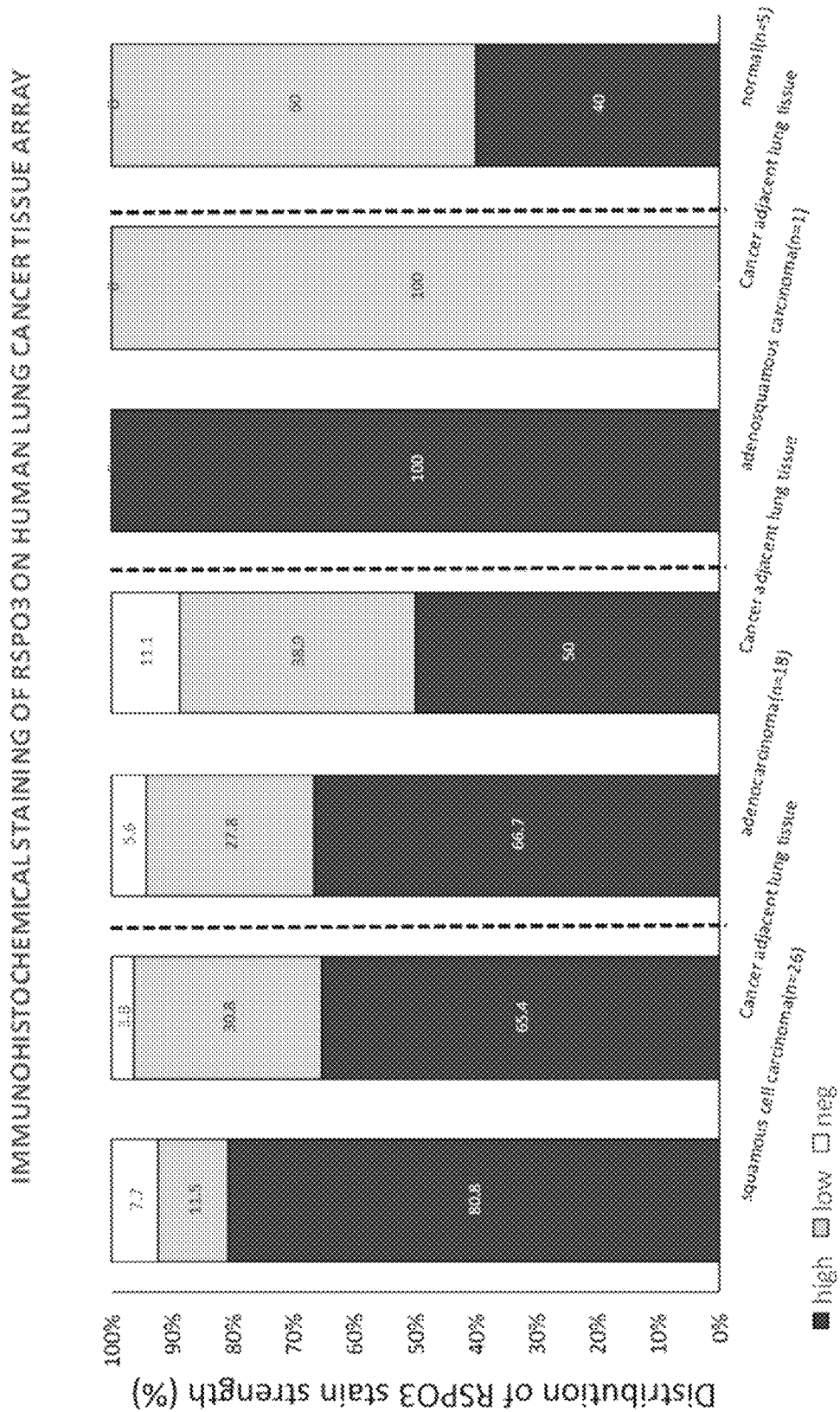
FIG. 17 is a graph showing expression of RSPO3 in lung cancer tissues. A lung cancer tissue microarray consisting of 50 patient samples was stained with the anti-RSPO3 mAb hB1. Images of whole sections were scanned by 3DHISTECH's digital slide scanner. The graph shows the percentages of cases expressing RSPO3 in the cancer tissue array and normal tissue array.

The expression of RSPO3 in a 50 lung non-small cell carcinoma and normal cases tissue array was evaluated by RSPO3 antibody hB1. The results showed that 92.3% (24/26) of tumors showed low to strong RSPO3 positive staining, while only 7.7% (2/26) showed negative staining n squamous cell carcinoma cases. See FIG. 17.

Figure 18:
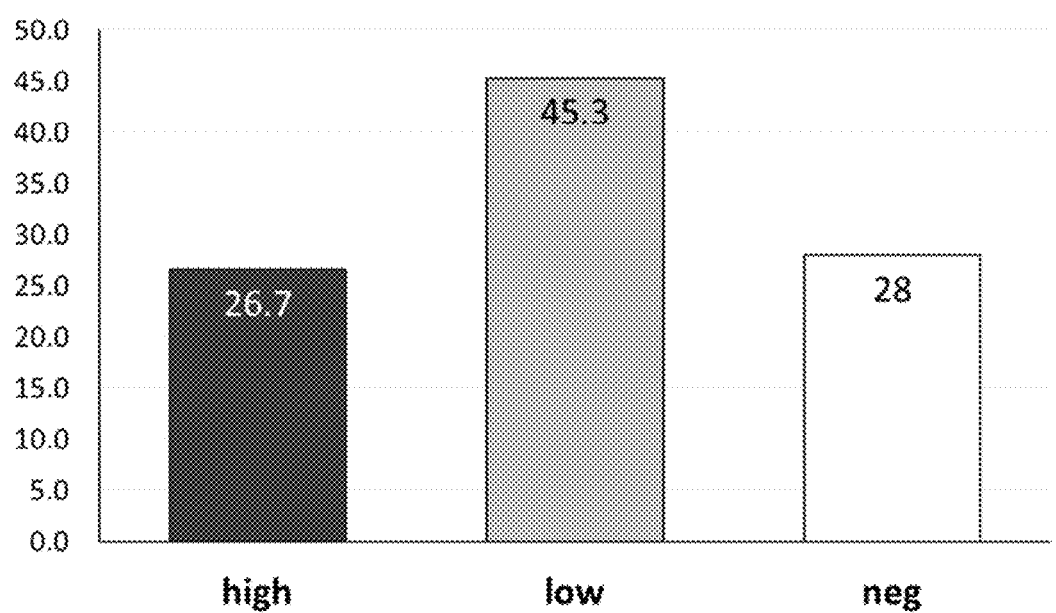
FIG. 18 is a graph showing expression of RSPO3 in breast cancer tissues. A breast cancer tissue microarray consisting of 75 patient samples was stained with the anti-RSPO3 mAb hB1. Images of whole sections were scanned by 3DHISTECH's digital slide scanner. The graph shows the percentages of cases expressing RSPO3 in the breast invasive ductal carcinoma tissue array.

A breast invasive ductal carcinoma tissue array was evaluated for RSPO3 expression by RSPO3 antibody hB 1. The results showed that 72% (54/75) of the tumor samples showed low to strong RSPO3 positive staining, while only 28% (21/75) showed negative staining in the breast invasive ductal carcinoma cases. See FIG. 18.

Figure 19:
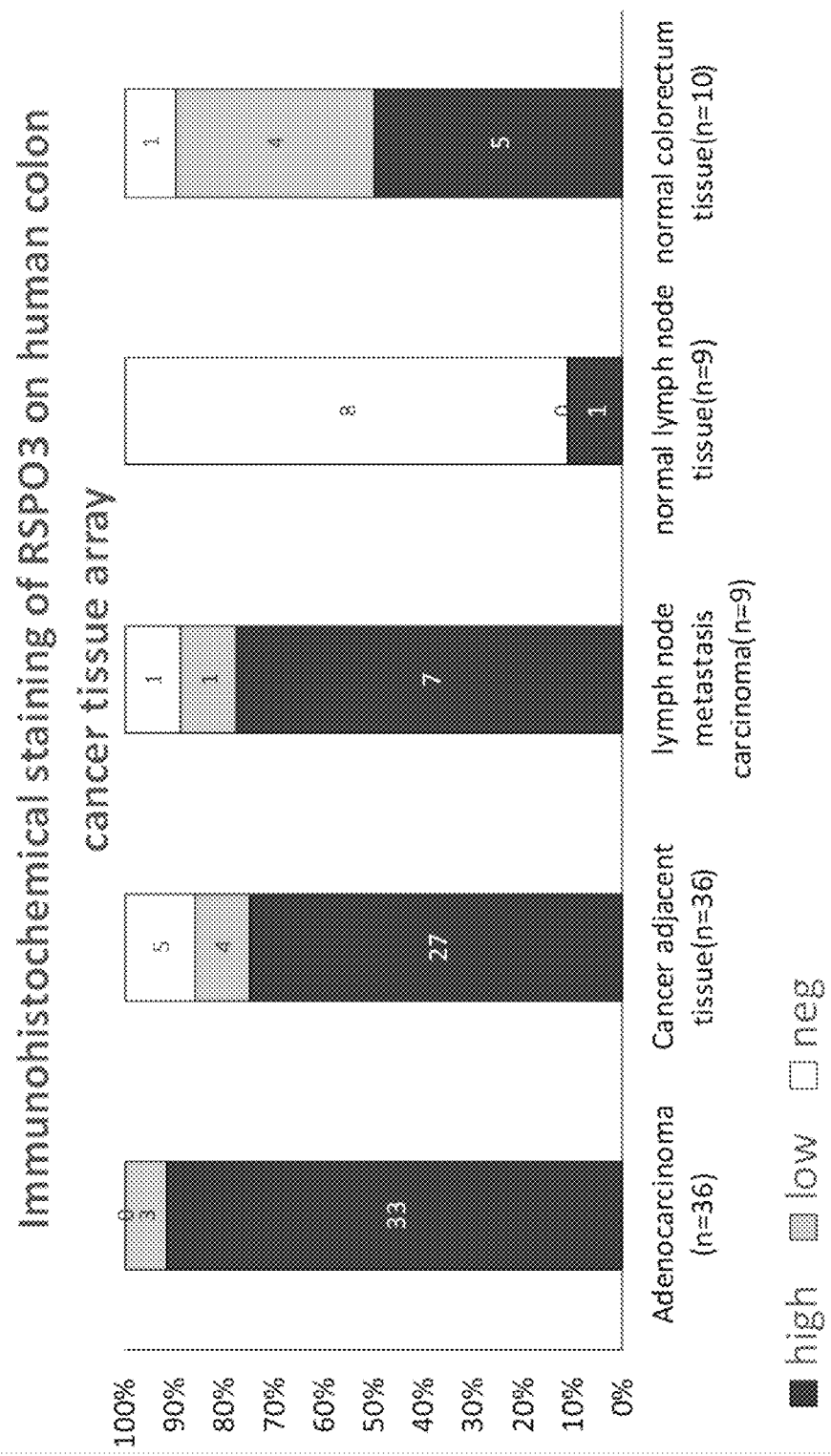
FIG. 19 is a graph showing expression of RSPO3 in colon cancer tissues. A colon cancer tissue microarray consisting of 64 patient samples was stained with the anti-RSPO3 mAb hB1. Images of whole sections were scanned by 3DHISTECH's digital slide scanner. The graph shows the percentages of cases expressing RSPO3 in the colorectal carcinoma tissue array.

The expression of RSPO3 in a 64 colorectal carcinoma and matched adjacent normal tissue microarray was evaluated by RSPO3 antibody hB1. The results showed that 91.7% (33/36) of the tumors showed strong RSPO3 positive staining, while only 8.3% (3/36) showed low staining in colorectal adenocarcinoma cases. See FIG. 19.

It was found that high RSPO3 staining detected by hB1 was significantly associated with distant metastases in patients with pancreatic cancer, lung cancer or breast cancer.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. An isolated antibody, comprising:
heavy chain complementary determining regions CDR1, CDR2, and CDR3 of a heavy chain variable region sequence from SEQ ID NO: 14; and
light chain complementary determining regions CDR1, CDR2, and CDR3 of a light chain variable region sequence from SEQ ID NO: 16;
wherein the antibody binds specifically to a R-spondin 3 (RSPO3) protein.

2. The antibody of claim 1, wherein the antibody includes a heavy chain variable region that is at least 80% identical to the sequence of SEQ ID NO: 14, and a light chain variable region that is at least 80% identical to the sequence of SEQ ID NO: 16.

3. The antibody of claim 1, wherein the antibody is an IgG antibody, an antibody that contains an Fc region, an Fab fragment, an Fab' fragment, an F(ab')₂ fragment, a single-chain antibody, an scFV multimer, a monovalent antibody, a multivalent antibody, or a chimeric antibody.

4. The antibody of claim 1, wherein the antibody is humanized.

5. The antibody of claim 1, wherein the antibody is conjugated to another molecule.

6. A composition, comprising the antibody of claim 1 and a pharmaceutically acceptable carrier.

7. The composition of claim 6, further comprising another therapeutic agent.

8. A method of inhibiting RSPO3 in a cell, comprising contacting the cell with an effective amount of the antibody of claim 1.

9. A method of inhibiting Wnt signaling in a cell, comprising contacting the cell with an effective amount of the antibody of claim 1.

10. A method of inhibiting cancer cell growth or cancer cell metastasis, comprising contacting the cell with an effective amount of the antibody of claim 1, wherein the cancer cell expresses an RSPO3 protein.

11. A method of detecting a RSPO3 protein or a fragment thereof in a sample, comprising:
contacting the sample with the antibody of claim 1;
assaying for specific binding between the antibody and a RSPO3 protein or a fragment thereof; and
detecting the RSPO3 protein or fragment thereof in the sample based on the specific binding.

12. The method of claim 11, wherein the RSPO3 protein is human RSPO3.

\* \* \* \* \*

SEQUENCE LISTING

```
<160> NUMBER OF SEQ ID NOS: 84

<210> SEQ ID NO 1
<211> LENGTH: 345
<212> TYPE: DNA
<213> ORGANISM: Artificial Sequence
<220> FEATURE:
<223> OTHER INFORMATION: Synthetic polynucleotide

<400> SEQUENCE: 1
caggtgcaac tgcaggagtc tggggctgaa ctggcaaaac ctggggcctc agtgaagatg     60
tcctgcaagg cttctggcca cactctaact tactactgga tgcactgggt aaaacagagg    120
cctggacagg gtctggaatg gattggatac attgatccta gcactggtta tagtgaatac    180
aatcaaagat tcgagggcaa ggccacattg actgcagaca agtcctccgg cacagtctac    240
atgcagctga gcagcctgac atctgaggac tctgcggtct attactgtgc aagaaacggg    300
ccctttgctt actggggcca agggactctg gtcactgtct ctgcg                    345

<210> SEQ ID NO 2
<211> LENGTH: 115
<212> TYPE: PRT
<213> ORGANISM: Artificial Sequence
<220> FEATURE:
<223> OTHER INFORMATION: heavy chain variable region

<400> SEQUENCE: 2

Gln Val Gln Leu Gln Glu Ser Gly Ala Glu Leu Ala Lys Pro Gly Ala
1               5                   10                  15

Ser Val Lys Met Ser Cys Lys Ala Ser Gly His Thr Leu Thr Tyr Tyr
                20                  25                  30

Trp Met His Trp Val Lys Gln Arg Pro Gly Gln Gly Leu Glu Trp Ile
            35                  40                  45

Gly Tyr Ile Asp Pro Ser Thr Gly Tyr Ser Glu Tyr Asn Gln Arg Phe
    50                  55                  60

Glu Gly Lys Ala Thr Leu Thr Ala Asp Lys Ser Ser Gly Thr Val Tyr
65                  70                  75                  80

Met Gln Leu Ser Ser Leu Thr Ser Glu Asp Ser Ala Val Tyr Tyr Cys
                85                  90                  95

Ala Arg Asn Gly Pro Phe Ala Tyr Trp Gly Gln Gly Thr Leu Val Thr
                100                 105                 110

Val Ser Ala
        115

<210> SEQ ID NO 3
<211> LENGTH: 321
<212> TYPE: DNA
<213> ORGANISM: Artificial Sequence
<220> FEATURE:
<223> OTHER INFORMATION: Synthetic polynucleotide
```

<400> SEQUENCE: 3

```
gacaatgttc tcacccagtc tccagcaatc atgtctgcat ctccagggga gaaggtcacc    60
atgacctgca gtgccagctc aagtgtaaat tacatgtact ggtaccagca gaagccggga   120
tcctccccca gactcctgat ttatgacaca tccaagctgg cttccggagt ccctgttcgc   180
ttcagtggca gtgggtctgg gacctcttac tctctcacaa tcagccgaat ggaggctgaa   240
gatgctgcca cttattattg ccagcagtgg agtagttccc cgctcacgtt cggtgttggg   300
gccaagctgg aaatcaaacg c                                             321
```

<210> SEQ ID NO 4
<211> LENGTH: 107
<212> TYPE: PRT
<213> ORGANISM: Artificial Sequence
<220> FEATURE:
<223> OTHER INFORMATION: Light chain variable region

<400> SEQUENCE: 4

```
Asp Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Pro Gly Ser Ser Pro Arg Leu Leu Ile Tyr
        35                  40                  45

Asp Thr Ser Lys Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Ser Pro Leu Thr
                85                  90                  95

Phe Gly Val Gly Ala Lys Leu Glu Ile Lys Arg
            100                 105
```

<210> SEQ ID NO 5
<211> LENGTH: 345
<212> TYPE: DNA
<213> ORGANISM: Artificial Sequence
<220> FEATURE:
<223> OTHER INFORMATION: Synthetic polynucleotide

<400> SEQUENCE: 5

```
caggtccaac tgcagcagtc tggggcagag attgtgaggt caggggcctc agtcaagttg    60
tcctgcacag cttctggctt cagtattaca gaatactata tacactgggt gaagcagagg   120
cctgatcagg gcctggagtg gataggaatg attgatcctg agaatggtga tactgactat   180
gccccgaagt tccagggcaa ggccactatg actgcagaca catcgtccaa tacagtcaac   240
ctgcaactca gcagcctgac atctgaggac actgccgtct attactgtca tggaccgggc   300
ccccttgagt actggggcca aggcaccact ctcacagtct cctcg                   345
```

<210> SEQ ID NO 6
<211> LENGTH: 115
<212> TYPE: PRT
<213> ORGANISM: Artificial Sequence
<220> FEATURE:
<223> OTHER INFORMATION: Heavy chain variable region

<400> SEQUENCE: 6

```
Gln Val Gln Leu Gln Gln Ser Gly Ala Glu Ile Val Arg Ser Gly Ala
1               5                   10                  15
```

Ser Val Lys Leu Ser Cys Thr Ala Ser Gly Phe Ser Ile Thr Glu Tyr
            20                  25                  30

Tyr Ile His Trp Val Lys Gln Arg Pro Asp Gln Gly Leu Glu Trp Ile
        35                  40                  45

Gly Met Ile Asp Pro Glu Asn Gly Asp Thr Tyr Ala Pro Lys Phe
    50                  55                  60

Gln Gly Lys Ala Thr Met Thr Ala Asp Thr Ser Ser Asn Thr Val Asn
65                  70                  75                  80

Leu Gln Leu Ser Ser Leu Thr Ser Glu Asp Thr Ala Val Tyr Tyr Cys
                85                  90                  95

His Gly Pro Gly Pro Leu Glu Tyr Trp Gly Gln Gly Thr Thr Leu Thr
            100                 105                 110

Val Ser Ser
    115

<210> SEQ ID NO 7
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 7
gacattgtaa tgacccaatc tccactctcc ctgcctgtca gtcttggaga tcaagcctcc      60
atctcttgta gatctagtca gagtattgta catagtaatg aaacactta tttagaatgg     120 tacctgcaga aaccaggcca gtctccaaac ctcctgatct acagagtttc caaccgcttt    180
tctggggtcc cagacaggtt caatggcagt ggatcaggga cagatttcac actcaagatc    240
agcagagtgg agcctgagga tctgggagtt tattcctgct ttcaagcttc acatgttccg    300
tacacgttcg gaggggggac caagctggaa ataaaacgc                           339

<210> SEQ ID NO 8
<211> LENGTH: 113
<212> TYPE: PRT
<213> ORGANISM: Artificial Sequence
<220> FEATURE:
<223> OTHER INFORMATION: Light chain variable region

<400> SEQUENCE: 8

Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Asn Leu Leu Ile Tyr Arg Val Ser Asn Arg Phe Ser Gly Val Pro
    50                  55                  60

Asp Arg Phe Asn Gly Ser Gly Ser Gly Thr Asp Phe Thr Leu Lys Ile
65                  70                  75                  80

Ser Arg Val Glu Pro Glu Asp Leu Gly Val Tyr Ser Cys Phe Gln Ala
                85                  90                  95

Ser His Val Pro Tyr Thr Phe Gly Gly Gly Thr Lys Leu Glu Ile Lys
            100                 105                 110

Arg

<210> SEQ ID NO 9

```
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 9
cagattcagc ttcaggagtc aggacctggc ctcgtgaaac cttctcagtc tctgtctctc      60
acctgctctg tcactggcta ctcaataacc agtggttatt attggaattg gatccggcag     120
tttccaggaa ataaactgga atggatgggc tacataagtt acgacggtac caataactac     180
aacccatctc tcaaagatcg aatctccatc actcgtgaca catctatgaa ccagttttc      240 ctgaagttga attctgtgac tactgaggac acagctacat attactgttc agtcttatta     300
atacagtact tcaatatctg gggcgccgga accacggtca ccgtctcctc g              351

<210> SEQ ID NO 10
<211> LENGTH: 117
<212> TYPE: PRT
<213> ORGANISM: Artificial Sequence
<220> FEATURE:
<223> OTHER INFORMATION: Heavy chain variable region

<400> SEQUENCE: 10

Gln Ile Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Thr Asn Asn Tyr Asn Pro Ser Leu
    50                  55                  60

Lys Asp Arg Ile Ser Ile Thr Arg Asp Thr Ser Met Asn Gln Phe Phe
65                  70                  75                  80

Leu Lys Leu Asn Ser Val Thr Thr Glu Asp Thr Ala Thr Tyr Tyr Cys
                85                  90                  95

Ser Val Leu Leu Ile Gln Tyr Phe Asn Ile Trp Gly Ala Gly Thr Thr
            100                 105                 110

Val Thr Val Ser Ser
        115

<210> SEQ ID NO 11
<211> LENGTH: 324
<212> TYPE: DNA
<213> ORGANISM: Artificial Sequence
<220> FEATURE:
<223> OTHER INFORMATION: Synthetic polynuceotide

<400> SEQUENCE: 11
gacatccaga tgacacagtc tccagcctcc ctatctgcat ctgtgggaga accgtcacc       60 atcacatgtc gaacaagtga gagtgttaac aatttcttag cctggtttca ccagaaacag    120
ggaaaatctc ctcaactcct ggtctatcat gcaaaaacct agcagatggt gtgtcatca     180 aggttcagtg gcagtggatc aggaacacaa tattctctca agatcaacag cctgcagcct    240
gaagattttg ggaattatta ctgtcaacat ttttggagta ttccgtggac gttcggtgga    300
ggcaccaagc tggaaatcaa acgc                                             324

<210> SEQ ID NO 12
<211> LENGTH: 108
```

```
<212> TYPE: PRT
<213> ORGANISM: Artificial Sequence
<220> FEATURE:
<223> OTHER INFORMATION: Light chain variable region

<400> SEQUENCE: 12

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Ser Val Asn Asn Phe
            20                  25                  30

Leu Ala Trp Phe His Gln Lys Gln Gly Lys Ser Pro Gln Leu Leu Val
        35                  40                  45

Tyr His Ala Lys Thr Leu Ala Asp Gly Val Ser Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Asn Tyr Tyr Cys Gln His Phe Trp Ser Ile Pro Trp
                85                  90                  95

Thr Phe Gly Gly Gly Thr Lys Leu Glu Ile Lys Arg
            100                 105

<210> SEQ ID NO 13
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 13
cagatccagc tccaagagag cggccccggc ctggtgaagc ccagcgagag cctgagcctg      60
acctgctcgg tgaccggcta cagcatcacc agcggctact actggaactg gatcaggcag     120
ttccccggca acggcctgga gtggatgggc tacatcagct acgacggcac caacaactac     180
aaccccagcc tgaaggacag gatcagcatc accaggacac cagcaagaa ccagttcttc      240 ctgaagctga acagcgtgac cgccgccgac accgccacct actactgctc ggtgctgctg     300
atccagtact tcaacatctg gggcaagggc accaccgtga ccgtgagcag c              351

<210> SEQ ID NO 14
<211> LENGTH: 117
<212> TYPE: PRT
<213> ORGANISM: Artificial Sequence
<220> FEATURE:
<223> OTHER INFORMATION: Heavy chain variable region

<400> SEQUENCE: 14

Gln Ile Gln Leu Gln Glu Ser Gly Pro Gly Leu Val Lys Pro Ser Glu
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Gly Leu Glu Trp
        35                  40                  45

Met Gly Tyr Ile Ser Tyr Asp Gly Thr Asn Asn Tyr Asn Pro Ser Leu
    50                  55                  60

Lys Asp Arg Ile Ser Ile Thr Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Ser Val Leu Leu Ile Gln Tyr Phe Asn Ile Trp Gly Lys Gly Thr Thr
```

Val Thr Val Ser Ser
    115

<210> SEQ ID NO 15
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 15
gacatccaga tgacccagag ccccagcagc ctgagcgcca gcgtgggcga gagggtgacc      60
atcacctgcc gtaccagcga gagcgtgaac aacttcctgg cctggttcca ccagaagccc     120
ggcaagagcc ccaagctgct ggtgtaccac gccaagaccc tggccgacgg cgtgagcagc     180
aggttcagcg gcagcggcag cggcacccag tacagcctga agatcaacag cctgcaaccc     240
gaggacttcg gcaactacta ctgccagcac ttctggagca tcccctggac cttcggcggc     300
ggcaccaagc tggagatcaa gagg                                            324

<210> SEQ ID NO 16
<211> LENGTH: 108
<212> TYPE: PRT
<213> ORGANISM: Artificial Sequence
<220> FEATURE:
<223> OTHER INFORMATION: Light chain variable region

<400> SEQUENCE: 16

Asp Ile Gln Met Thr Gln Ser Pro Ser Ser Leu Ser Ala Ser Val Gly
1               5                   10                  15

Glu Arg Val Thr Ile Thr Cys Arg Thr Ser Glu Ser Val Asn Asn Phe
            20                  25                  30

Leu Ala Trp Phe His Gln Lys Pro Gly Lys Ser Pro Lys Leu Leu Val
        35                  40                  45

Tyr His Ala Lys Thr Leu Ala Asp Gly Val Ser Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Asn Tyr Tyr Cys Gln His Phe Trp Ser Ile Pro Trp
                85                  90                  95

Thr Phe Gly Gly Gly Thr Lys Leu Glu Ile Lys Arg
            100                 105

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
gacawtgttc tcacccagtc                                                  20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18

```
gacatccaga tgacacagwc                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
gatrttgtga tgacccagwc                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gacattstgm tgacccagtc                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gatgttgtgv tgacccaaac                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
gacacaactg tgacccagtc                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
gayattktgc tcactcagtc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
gatattgtga tracccaggm                                              20

<210> SEQ ID NO 25
<211> LENGTH: 20
<212> TYPE: DNA
```

<213> ORGANISM: Artificial Sequence
<220> FEATURE:
<223> OTHER INFORMATION: Synthetic oligonucleotide

<400> SEQUENCE: 25
gacattgtaa tgacccaatc                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
gacattgtga tgwcacagtc                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
gatrtccaga tgamccagtc                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
gatggagaaa caacacaggc                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
gacgctgttg tgactcagga                                               20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
gaccytgtgc tcactcagtc                                               20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
gcgtttbatt tccagcttgg                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
gcgttttatt tccaattttg                                               20

<210> SEQ ID NO 33
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 33
gcctaggaca gtcamcytg                                                19

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
gaggttcdsc tgcaacagty                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
caggtgcaam tgmagsagtc                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
gavgtgmwgc tggtggagtc                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
caggttaytc tgaaagagtc                                               20

<210> SEQ ID NO 38
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 38
gakgtgcagc ttcagsagtc                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
cagatccagt tsgygcagtc                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
cagrtccaac tgcagcagyc                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gaggtgmagc tasttgagwc                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
gaagtgaagm ttgaggagtc                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
gatgtgaacc tggaagtgtc                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
cagatkcagc ttmaggagtc                                               20

```
<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
caggcttatc tgcagcagtc                                                   20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
caggttcacc tacaacagtc                                                   20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
caggtgcagc ttgtagagac                                                   20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
gargtgmagc tgktggagac                                                   20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
cgaggagacg gtgacmgtgg                                                   20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
cgcagagaca gtgaccagag                                                   20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 51
cgaggagact gtgagastgg                                              20

<210> SEQ ID NO 52
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 52
catgcctagg ccaccatgta caggatgcaa ctcctgtc                          38

<210> SEQ ID NO 53
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 53
gggtttcata tgtcatttac ccggagacag g                                 31

<210> SEQ ID NO 54
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 54
ggaagatatc ccaccatgta caggatgcaa ctcctgtc                          38

<210> SEQ ID NO 55
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 55
ccttaattaa ctaacactct cccctgttga agc                               33

<210> SEQ ID NO 56
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 56
gaaggtgaag gtcggagtc                                               19

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
gaagatggtg atgggatttc                                              20

<210> SEQ ID NO 58
<211> LENGTH: 19
```

```
<212> TYPE: DNA
<213> ORGANISM: Artificial Sequence
<220> FEATURE:
<223> OTHER INFORMATION: Synthetic oligonucleotide

<400> SEQUENCE: 58
tgatgaccat tgcctacac                                                  19

<210> SEQ ID NO 59
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 59
gtaaggttta ttaaagagga gaag                                            24

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
tccccacctt gaatgaagaa                                                 20

<210> SEQ ID NO 61
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 61
tggtggctgg tgcaaaga                                                   18

<210> SEQ ID NO 62
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 62
cacccggcca ttgtgc                                                     16

<210> SEQ ID NO 63
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 63
gcttttccct cgaccgc                                                    17

<210> SEQ ID NO 64
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 64
```
gcattggcat cttctatggt t                                            21

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
cgccttgtcc ttggtagtgt                                              20

<210> SEQ ID NO 66
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 66
tccaacacct cccagtatga ca                                           22

<210> SEQ ID NO 67
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 67
tcttcaggat tcgttctgta tt                                           22

<210> SEQ ID NO 68
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 68
gccaaacagt gcccagacc                                               19

<210> SEQ ID NO 69
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 69
ctctcgaccg ttgtgtgcg                                               19

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
acgccagaac aacgaatacc                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
acgaccttgc catccactac        20

<210> SEQ ID NO 72
<211> LENGTH: 277
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(277)
<223> OTHER INFORMATION: mRSPO3

<400> SEQUENCE: 72

Met His Leu Arg Leu Ile Ser Cys Phe Phe Ile Ile Leu Asn Phe Met
1               5                   10                  15

Glu Tyr Ile Gly Ser Gln Asn Ala Ser Arg Gly Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Val
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Val Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Ser
        115                 120                 125

Cys Pro Glu Gly Leu Glu Ala Asn Asn His Thr Met Glu Cys Val Ser
    130                 135                 140

Ile Val His Cys Glu Ala Ser Glu Trp Ser Pro Trp Ser Pro Cys Met
145                 150                 155                 160

Lys Lys Gly Lys Thr Cys Gly Phe Lys Arg Gly Thr Glu Thr Arg Val
                165                 170                 175

Arg Asp Ile Leu Gln His Pro Ser Ala Lys Gly Asn Leu Cys Pro Pro
            180                 185                 190

Thr Ser Glu Thr Arg Thr Cys Ile Val Gln Arg Lys Lys Cys Ser Lys
        195                 200                 205

Gly Glu Arg Gly Lys Lys Gly Arg Glu Arg Lys Arg Lys Lys Leu Asn
    210                 215                 220

Lys Glu Glu Arg Lys Glu Thr Ser Ser Ser Asp Ser Lys Gly Leu
225                 230                 235                 240

Glu Ser Ser Ile Glu Thr Pro Asp Gln Gln Asn Lys Glu Arg Gln
                245                 250                 255

Gln Gln Gln Lys Arg Arg Ala Arg Asp Lys Gln Gln Lys Ser Val Ser
            260                 265                 270

Val Ser Thr Val His
        275

<210> SEQ ID NO 73
<211> LENGTH: 272
<212> TYPE: PRT

<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(272)
<223> OTHER INFORMATION: hRSPO3

<400> SEQUENCE: 73

```
Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Gln Arg Arg
            20                  25                  30

Met His Pro Asn Val Ser Gln Gly Cys Gln Gly Gly Cys Ala Thr Cys
            35                  40                  45

Ser Asp Tyr Asn Gly Cys Leu Ser Cys Lys Pro Arg Leu Phe Phe Ala
        50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
            115                 120                 125

Cys Pro Glu Gly Leu Glu Ala Asn Asn His Thr Met Glu Cys Val Ser
130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
        195                 200                 205

Gly Glu Arg Gly Lys Gly Arg Glu Arg Lys Arg Lys Lys Pro Asn
210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Lys Lys
                245                 250                 255

Arg Lys Val Gln Asp Lys Gln Lys Ser Val Ser Val Ser Thr Val His
            260                 265                 270
```

<210> SEQ ID NO 74
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 74

```
Gln Asn Ala Ser Arg Gly Arg Arg Gln Arg
1               5                   10
```

<210> SEQ ID NO 75
<211> LENGTH: 10
<212> TYPE: PRT
<213> ORGANISM: Artificial Sequence

```
<220> FEATURE:
<223> OTHER INFORMATION: Synthetic polypeptide

<400> SEQUENCE: 75

Ala Ser Arg Gly Arg Gln Arg Arg Met
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 76

Arg Arg Gln Arg Arg Met His Pro Asn Val
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 77

Cys Leu Ser Cys Lys Pro Arg Leu Phe Phe
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 78

Ser Cys Lys Pro Arg Leu Phe Phe Ala Leu
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 79

Glu Arg Gly Lys Lys Gly Arg Glu Arg Lys
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 80

Gly Lys Lys Gly Arg Glu Arg Lys Arg Lys
1               5                   10

<210> SEQ ID NO 81
<211> LENGTH: 10
<212> TYPE: PRT
<213> ORGANISM: Artificial Sequence
<220> FEATURE:
```

```
-continued

<223> OTHER INFORMATION: Synthetic polypeptide

<400> SEQUENCE: 81

Lys Gly Arg Glu Arg Lys Arg Lys Lys Pro
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 82

Arg Glu Arg Lys Arg Lys Lys Pro Asn Lys
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 83

Arg Glu Asn Lys Gln Gln Gln Lys Lys Arg
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 84

Arg Gly Arg Arg Gln Arg Arg Met His Pro
1               5                   10
```